(12) United States Patent
Minamiguchi et al.

(10) Patent No.: US 8,735,170 B2
(45) Date of Patent: *May 27, 2014

(54) METHOD FOR MEASURING CONCENTRATION OF ANTIGEN CONTAINED IN TEST SOLUTION

(75) Inventors: Masaru Minamiguchi, Kyoto (JP); Tatsurou Kawamura, Kyoto (JP); Masahiko Shioi, Kyoto (JP); Atsushi Matsubara, Osaka (JP)

(73) Assignee: Panasonic Corporation, Osaka (JP)

( * ) Notice: Subject to any disclaimer, the term of this patent is extended or adjusted under 35 U.S.C. 154(b) by 163 days.

This patent is subject to a terminal disclaimer.

(21) Appl. No.: 13/483,790

(22) Filed: May 30, 2012

(65) Prior Publication Data

US 2012/0288960 A1 Nov. 15, 2012

Related U.S. Application Data

(63) Continuation of application No. PCT/JP2011/005128, filed on Sep. 12, 2011.

(30) Foreign Application Priority Data

Sep. 13, 2010 (JP) ................................. 2010-204148

(51) Int. Cl.
| | |
|---|---|
| *G01N 33/566* | (2006.01) |
| *G01N 33/551* | (2006.01) |
| *G01N 33/553* | (2006.01) |
| *G01N 21/64* | (2006.01) |

(52) U.S. Cl.
CPC ............ *G01N 33/551* (2013.01); *G01N 33/553* (2013.01); *G01N 21/648* (2013.01)
USPC ........................................................ 436/501

(58) Field of Classification Search
None
See application file for complete search history.

(56) References Cited

U.S. PATENT DOCUMENTS

| | | | |
|---|---|---|---|
| 7,884,934 B2 * | 2/2011 | Minamiguchi et al. | 356/365 |
| 8,085,405 B2 * | 12/2011 | Ogawa | 356/445 |

(Continued)

FOREIGN PATENT DOCUMENTS

| | | |
|---|---|---|
| JP | 2002-228662 | 8/2002 |
| JP | 2010-185738 | 8/2008 |

OTHER PUBLICATIONS

Holmseth et al., Specificity controls for immunocytochemistry, Anatomy and Embryology, vol. 211, Issue 4, pp. 257-266, Aug. 2006.*

(Continued)

*Primary Examiner* — Chris L Chin
*Assistant Examiner* — Richard Moerschell
(74) *Attorney, Agent, or Firm* — McDermott Will & Emery LLP

(57) ABSTRACT

A biogenic substance concentration measuring apparatus includes an optical measuring apparatus for measuring optical properties of a first substrate and a second substrate by using a cell for biogenic substance concentration measurement that includes: the first substrate on which a plurality of first metallic nanorods, each of which is modified with a substance that bonds specifically to a test substance, are immobilized such that the long axes thereof are aligned in the same direction; and the second substrate on which a plurality of second metallic nanorods, each of which is modified with a blocking substance, are immobilized such that the long axes thereof are aligned perpendicularly to the long axes of the first metallic nanorods on the first substrate, and calculates a biogenic substance concentration with high accuracy from the optical properties.

15 Claims, 20 Drawing Sheets

(56) References Cited

U.S. PATENT DOCUMENTS

2008/0160287 A1 7/2008 Misawa et al.
2009/0109422 A1* 4/2009 Handa et al. .................. 356/39
2010/0195106 A1 8/2010 Ogawa

OTHER PUBLICATIONS

International Search Report issued International Patent Application No. PCT/JP2011/005128 dated Jan. 2, 2012.

* cited by examiner

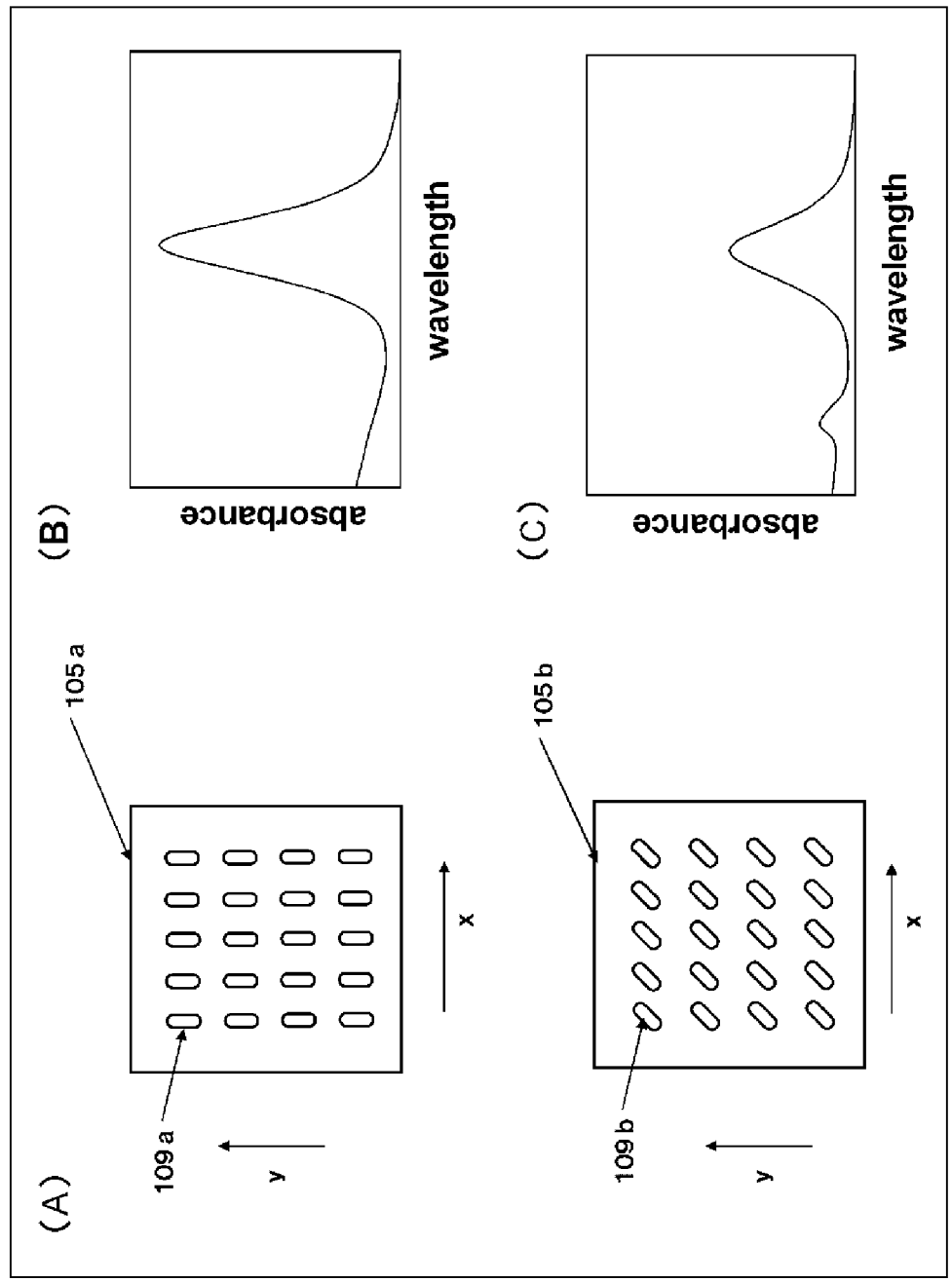

METHOD FOR MEASURING CONCENTRATION OF ANTIGEN CONTAINED IN TEST SOLUTION

RELATED APPLICATIONS

This is a continuation of International Application No. PCT/JP2011/005128, with an international filing date of Sep. 12, 2011, which claims priority of Japanese Patent Application No. 2010-204148, filed on Sep. 13, 2010, the contents of which are hereby incorporated by reference.

TECHNICAL FIELD

The present invention relates to a method for measuring a concentration of an antigen contained in a test solution, with use of surface plasmon resonance that occurs by irradiating metal with light.

BACKGROUND ART

Medical diagnosis, gene analysis, and the like are required to be conducted with promptness, high efficiency, and simplicity. Therefore recently, importance is given to a technology allowing highly-sensitive detection of a biogenic substance in very small amounts.

For example, surface plasmon resonance is used in a method for detecting biogenic substances such as proteins, hormones and low molecular weight compounds contained in test solutions of blood, perspiration, urine, or the like. Surface plasmon resonance occurs by free electrons in a metal interacting with electromagnetic waves (light). A detection method using surface plasmon resonance does not require labeling of the biogenic substance and is simple, differing from a fluorescence detection method and an electrochemical method.

Examples of surface plasmon resonance include propagating surface plasmon resonance and localized surface plasmon resonance.

A sensor using propagating surface plasmon resonance has, for example, a triangular prism. A thin metallic film is formed on one of the faces of the triangular prism. From a different face of the prism, light is applied to the face having the thin metallic film. When light enters into the thin metallic film from a certain angle, propagating surface plasmon resonance occurs. This certain angle is referred to as the resonance angle. The resonance angle depends on the refractive index (permittivity) of a material that is present near the thin metallic film (about 100 nm). Therefore, the propagating surface plasmon resonance sensor can highly sensitively detect changes in property of a nearby material.

When propagating surface plasmon resonance is used in a biosensor, antibodies are immobilized on the surface of the thin metallic film. By bringing a test solution containing biogenic substances (antigens) into contact with the surface of the thin metallic film, the antigen and the antibody react with and bond to each other. Since the refractive index near the thin metallic film changes, the resonance angle changes. If a correlation is obtained in advance between the concentration of antigens contained in the test solution and the resonance angle, the antigen concentration can be calculated from the change in the resonance angle.

Patent Literature 1 discloses a method that uses localized surface plasmon resonance. According to Patent Literature 1, dielectric particulates coated with noble metal (hereinafter, referred to as "particulates") are formed in a plurality of regions of the substrate surface. Antibodies that bond to biomolecules are immobilized on particulates formed in one region (hereinafter, referred to as "signal region"). The signal region indicates a resonant wavelength reflecting the concentration of the biomolecules. Particulates formed in another region (hereinafter, "reference region") are treated such that bonding to biomolecules is prevented from occurring. By irradiation with light, localized surface plasmon resonance is observed in each region. In the signal region, bonding to the biomolecules changes a reflectance spectrum. Meanwhile, in the reference region, biomolecules do not bond, and thus a reflectance spectrum does not change. An amount of reflectance spectrum change caused by bonding to the biomolecules can be obtained on the basis of the difference between the reflectance spectrum in the signal region and the reflectance spectrum in the reference region. The concentration of the biomolecules is calculated on the basis of the amount of the reflectance spectrum change.

CITATION LIST

Patent Literature

PTL 1: Japanese Patent No. 3528800

SUMMARY OF INVENTION

Technical Problem

The concentration of a test substance is highly sensitively detected with a conventional localized surface plasmon sensor having a signal region and a reference region on a surface thereof. However, since light is applied to the two detection regions, namely, the signal region and the reference region, it is necessary to move at least either one of a light source or a substrate. In order to maintain or improve measurement accuracy, the positions of the light source, the detection regions, and a photodetector have to be controlled with high accuracy. Therefore, movement of the light source or the substrate can decrease measurement accuracy.

An object of the present invention is to provide a method for measuring a concentration of an antigen contained in a test solution, which has improved accuracy with moving neither a light source nor a substrate.

Solution to Problem

A method for measuring a concentration of a first antigen contained in a test solution, by using an apparatus for measuring a concentration of a biogenic substance, the method comprising the following steps (a) to (h):
step (a) of preparing the apparatus,
the apparatus comprising:
a cell comprising therein a first region, a second region, and a space for retaining the test solution;
a light source;
a polarizing plate for polarizing light emitted from the light source; and
a photoreceiver for receiving light which has passed through the cell along an optical axis that intersects the first region, the second region, and the space for retaining the test solution, wherein
a plurality of first metallic nanorods each having a first antibody on a surface thereof are immobilized on the first region,
a plurality of second metallic nanorods each having a blocking substance on a surface thereof are immobilized on the second region, the long axes of the plurality of first metallic nanorods are aligned in the same direction, the long axes of the plurality of second metallic nanorods are aligned in the same direction, the long-axis direction of the first metallic nanorods is orthogonal to the long-axis direction of the second metallic nanorods, and at least either one of the polarizing plate or the cell is rotatable about the optical axis;

step (b) of supplying the test solution to the space for retaining the test solution to allow the first antigen to be bound to the first antibody and not to allow the first antigen to be bound to the blocking substance;

step (c) of transmitting polarized light parallel to the long-axis direction of the plurality of first metallic nanorods through the cell along the optical axis to receive resultant first light with the photoreceiver;

step (d) of calculating an amount $$\Delta\lambda a \qquad [\text{Chem.01}]$$

of shift of a localized surface plasmon resonant wavelength caused by binding the first antigen to the antibody, on the basis of the first light;

step (e) of rotating at least either one of the polarizing plate or the cell such that polarized light which has passed through the polarizing plate is parallel to the long-axis direction of the plurality of second metallic nanorods;

step (f) of transmitting polarized light parallel to the long-axis direction of the plurality of second metallic nanorods through the cell along the optical axis to receive resultant second light with the photoreceiver;

step (g) of calculating an amount $$\Delta\lambda b \qquad [\text{Chem.02}]$$

of shift of the localized surface plasmon resonant wavelength caused by supplying the test solution being supplied to the space for retaining the test solution, on the basis of the second light; and step (h) of calculating the concentration of the first antigen on the basis of a calibration curve and a difference represented by the following equation:

$$\text{the difference} = \Delta\lambda a - \Delta\lambda b. \qquad [\text{Chem.03}]$$

Advantageous Effects of Invention

The present invention provides a method for measuring a concentration of an antigen contained in a test solution. The method does not need movement of both a light source and a substrate and achieves improvement of measurement accuracy.

BRIEF DESCRIPTION OF DRAWINGS

FIG. 20(A) is an exploded diagram of the cell 105, FIG. 20(B) is a graph showing an absorption spectrum of the first substrate 105a when polarized light having a y direction is applied to the cell 105, and FIG. 20(C) is a graph showing an absorption spectrum of the second substrate 105b when the polarized light having the y direction is applied thereto.

DESCRIPTION OF EMBODIMENTS

Hereinafter, embodiments of the present invention will be described with reference to the drawings.

(Embodiment 1)

Embodiment 1 will be described with reference to FIGS. 1 to 3.

(Description of Apparatus 100)

Figure 1:
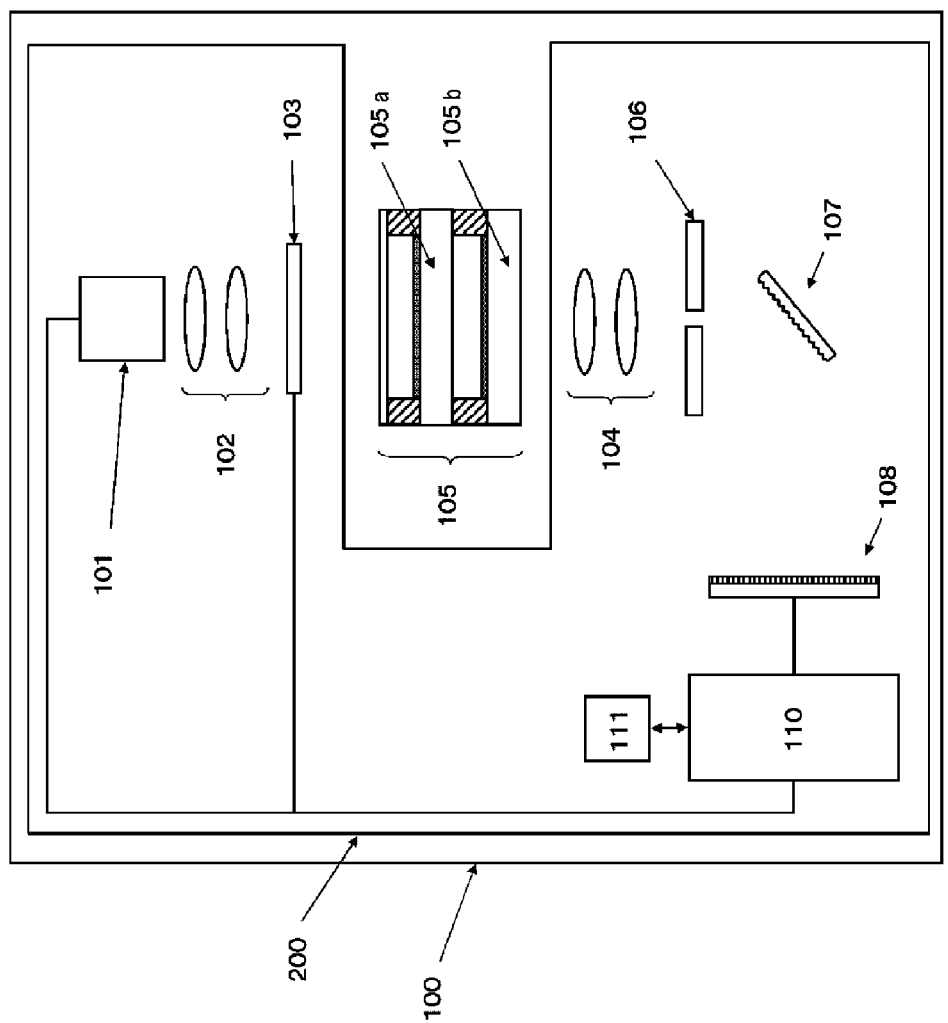
FIG. 1 is a diagram illustrating a configuration of a biogenic substance concentration measuring apparatus according to Embodiment 1.

FIG. 1 illustrates a configuration of an apparatus 100, for measuring the concentration of a biogenic substance, according to Embodiment 1. The apparatus 100 comprises a cell 105 and an optical measuring apparatus 200.

The optical measuring apparatus 200 comprises a light source 101, lenses 102, a polarizing plate 103, lenses 104, a slit 106, a grating device 107, a photoreceiver 108, and a microcomputer 110.

The light source 101 radiates light including a localized surface plasmon resonant wavelength. The light source 101 is preferably a halogen light source.

The lenses 102 (first lenses 102) adjust the light radiated from the light source 101.

The polarizing plate 103 polarizes the light that is radiated from the halogen light source 101 and adjusted by the lenses 102.

The lenses 104 (second lenses 104) adjust the light that has passed through the cell 105.

The slit 106 adjusts the light to substantially be in the form of a point light, when grating spectroscopy is performed.

The grating device 107 reflects the light that has passed through the slit 106 while the grating device 107 disperses the light according to the wavelengths.

The photoreceiver 108 has a plurality of photo-receptive regions and detects the dispersed light.

The microcomputer 110 (i.e., a calculation section) calculates the intensity of the light received by the photoreceiver 108. The microcomputer 110 calculates a localized surface plasmon resonant wavelength from the calculated intensity. The micro-computer 110 calculates the concentration of a test substance on the basis of the calculated localized surface plasmon resonant wavelength.

The cell 105 retains a test solution. The cell 105 comprises a first substrate 105a and a second substrate 105b. The first substrate 105a comprises a plurality of first metallic nanorods having long axes that are aligned in the same direction. Each metallic nanorod has a short axis of about 2 nm to 100 nm and a long axis of about 50 nm to 500 nm. The second substrate 105b comprises a plurality of second metallic nanorods, similarly to the first substrate 105a.

The first substrate 105a and the second substrate 105b correspond to a first region and a second region, respectively. The metallic nanorods can be formed on the entirety or a part of a surface of the substrate.

An example of the photoreceiver 108 is a CCD (charge coupled device), a CMOS, or a one-dimensional photodetector array. The photoreceiver 108 preferably comprises a plurality of photo-receptive regions.

An example of the polarizing plate 103 is a polarizing film formed of organic molecules.

At least either one of the polarizing plate 103 or the cell 105 rotates about an optical axis. Needless to say, the optical axis is parallel to the normal direction of the first substrate 105a.

The optical measuring apparatus 200 preferably includes a memory 111. The memory 111 stores wavelength data corresponding to each photo-receptive region of the photoreceiver 108 and data concerning the correlation between an amount of shift of the localized surface plasmon resonant wavelength and a biogenic substance concentration (i.e., a calibration curve).

Figure 2:
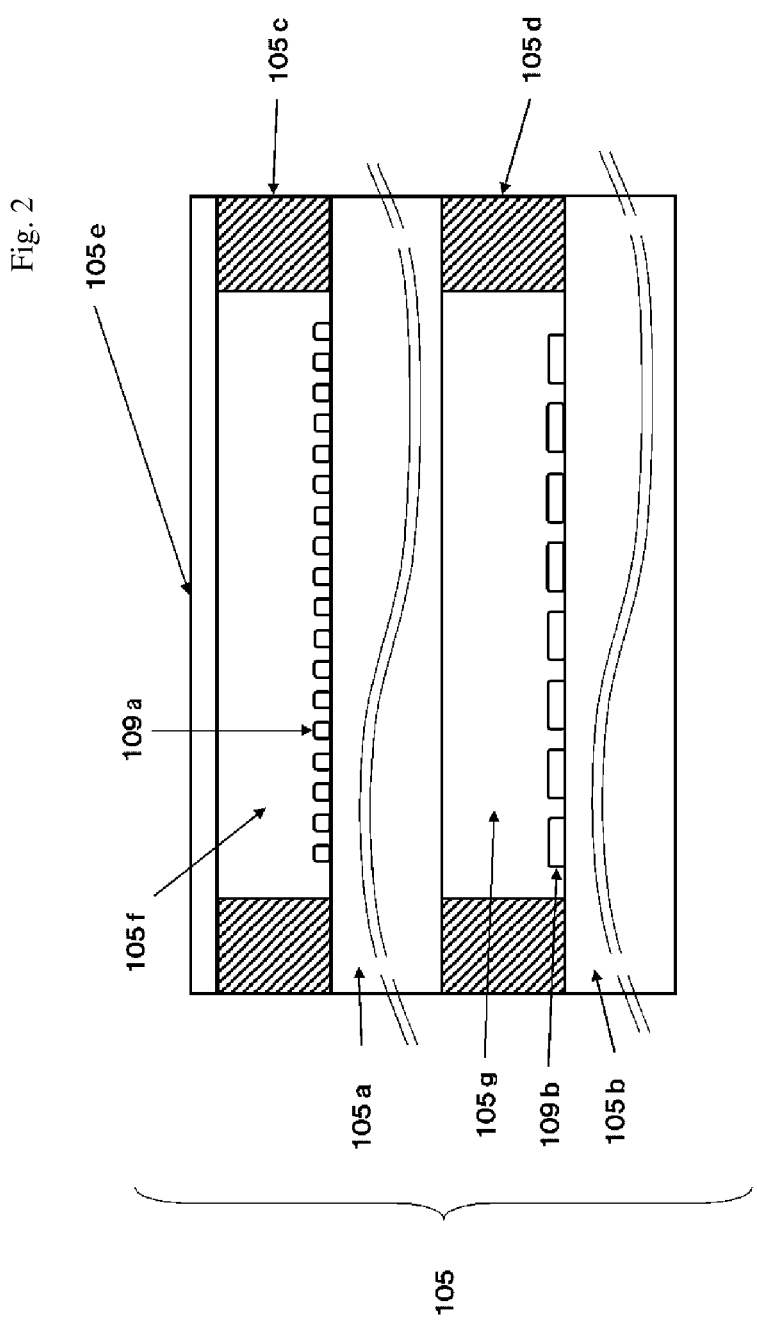
FIG. 2 is a diagram illustrating a cross section of a cell 105 according to Embodiment 1.

FIG. 2 illustrates the cell 105 according to Embodiment 1.

The cell 105 comprises the first substrate 105a, the second substrate 105b, a first spacer 105c, a second spacer 105d, and a cover glass 105e. The first substrate 105a comprises a plurality of first metallic nanorods 109a. The second substrate 105b comprises a plurality of second metallic nanorods 109b.

As shown in FIG. 2, a first test solution retention space 105f is surrounded by the first substrate 105a, the first spacer 105c, and the cover glass 105e. Similarly, a second test solution retention space 105g is surrounded by the first substrate 105a, the second spacer 105d, and the second substrate 105b. Each of the first test solution retention space 105f and the second test solution retention space 105g comprises a supply inlet and a drain outlet (not shown) for the test solution.

The materials of the first substrate 105a, the second substrate 105b, and the cover glass 105e are not particularly limited as long as the light from the light source 101 is allowed to pass therethrough. The materials are preferably $SiO_2$.

Figure 3:
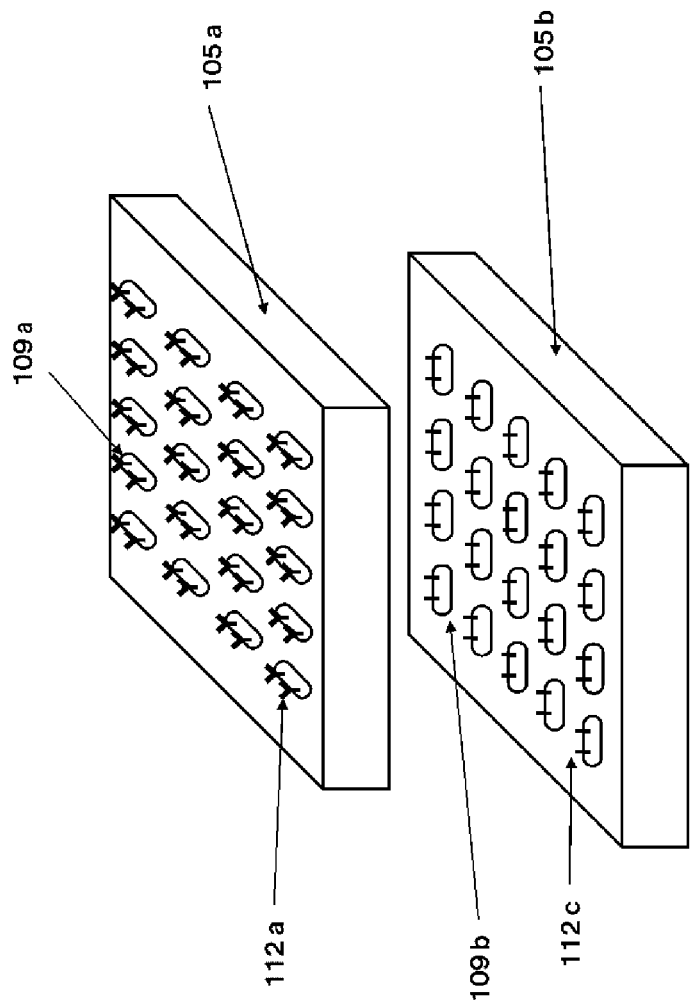
FIG. 3 is a perspective view of a part of the cell 105 according to Embodiment 1.

FIG. 3 illustrates the first substrate 105a and the second substrate 105b.

The first substrate 105a comprises the plurality of first metallic nanorods 109a having the long axes that are aligned in the same direction. The plurality of first metallic nanorods 109a may collectively be referred to as "first metallic nanorod group".

The second substrate 105b comprises the plurality of second metallic nanorods 109b having the long axes that are aligned in the same direction. The plurality of second metallic nanorods 109b may collectively be referred to as "second metallic nanorod group". The long axes of the plurality of first metallic nanorods 109a are orthogonal to the long axes of the plurality of second metallic nanorods 109b.

The plurality of first metallic nanorods 109a are modified with a first antibody 112a to form a measurement region. Meanwhile, the plurality of second metallic nanorods 109b are modified with a blocking substance 112c to form a reference region. None of antigens, proteins, and peptides bond to the blocking substance 112c. The antigens include a test substance contained in a test solution. The proteins include albumin and globulin.

An example of the blocking substance 112c is ovalbumin, bovine serum albumin, casein, skim milk, MPC (2-methacryloyloxyethyl phosphorylcholine) polymers having phospholipid polar groups at the side chains thereof, MPC polymer-containing polymers, or MPC polymer-containing copolymers.

The surface of the first substrate 105a and the surface of the second substrate 105b on which the plurality of first metallic nanorods 109a and the second metallic nanorods 109b are formed, respectively, face in the same direction.

(Substrate Fabricating Method)

A method for fabricating the first substrate 105a and the second substrate 105b is not particularly limited. For example, a fine structure is drawn by using x-ray lithography or electron-beam lithography. Next, metal is sputtered to fabricate a substrate 105.

A mold is prepared on an Si substrate by using x-ray lithography or electron-beam lithography. Nanorods are prepared on a resin by using nano-printing technology. Metal is sputtered to prepare metallic nanorods, whereby a substrate 105 is fabricated.

Metallic nanorods synthesized by a synthesis method using chemical reactions or a synthesis method using photoreactions are used, and a substrate 105 can be fabricated.

Shear stress is applied in a predetermined direction to a composition containing metallic nanorods, whereby the long axes of the metallic nanorods can be aligned in the same direction. More particularly, a composition containing a dispersant, a solvent, a resin, and metallic nanorods is applied to a substrate. By using a micro-gravure coater, the composition can be applied while a certain amount of shear stress is applied in a direction opposite to that of the substrate movement. Alternatively, an electric or magnetic force may be applied in a predetermined direction to the substrate during or after application of the composition, whereby the long axes can be aligned in the same direction.

The material of the metallic nanorods 109 is silver, gold, copper, aluminum, or platinum. A plurality of materials can be used. The metallic nanorods exhibit two localized surface plasmon resonance bands. One of the localized surface plasmon resonance bands originates from the short-axis direction. When Au nanorods are used, the one of the localized surface plasmon resonance bands appears at a wavelength near 520 nm. Meanwhile, the other localized surface plasmon resonance band originates from the long axis. When Au nanorods are used, the other localized surface plasmon resonance band appears at a wavelength of 600 to 1500 nm.

(Description of Absorption Spectrum)

Figure 4:
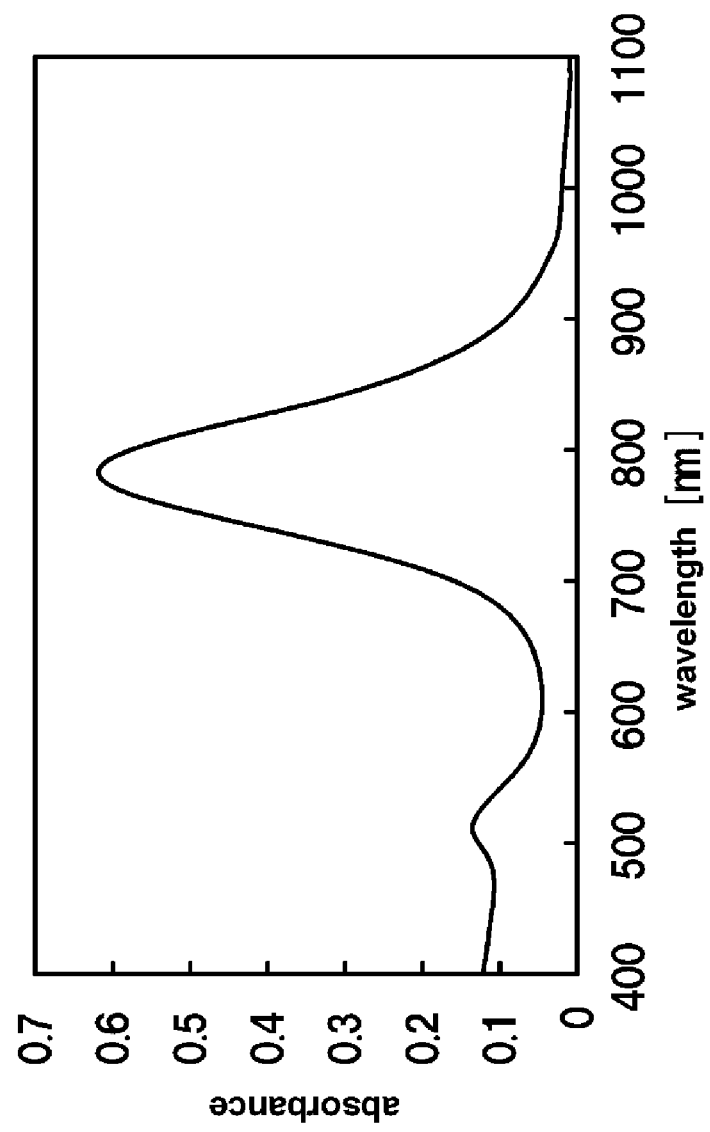
FIG. 4 is a diagram showing an absorption spectrum of Au nanorods.

FIG. 4 shows an absorption spectrum of Au nanorods each having an average short axis length of 10 nm and an average long axis length of 37 nm. The peak near a wavelength of 510 nm is a localized surface plasmon resonance band originating from the short axis. The peak near a wavelength of 780 nm is a localized surface plasmon resonance band originating from the long axis. An absorption peak wavelength in a localized surface plasmon resonance band is referred to as localized surface plasmon resonant wavelength.

In Embodiment 1, the localized surface plasmon resonant wavelength originating from the long axis is preferably 700 to 1000 nm.

Figure 5:
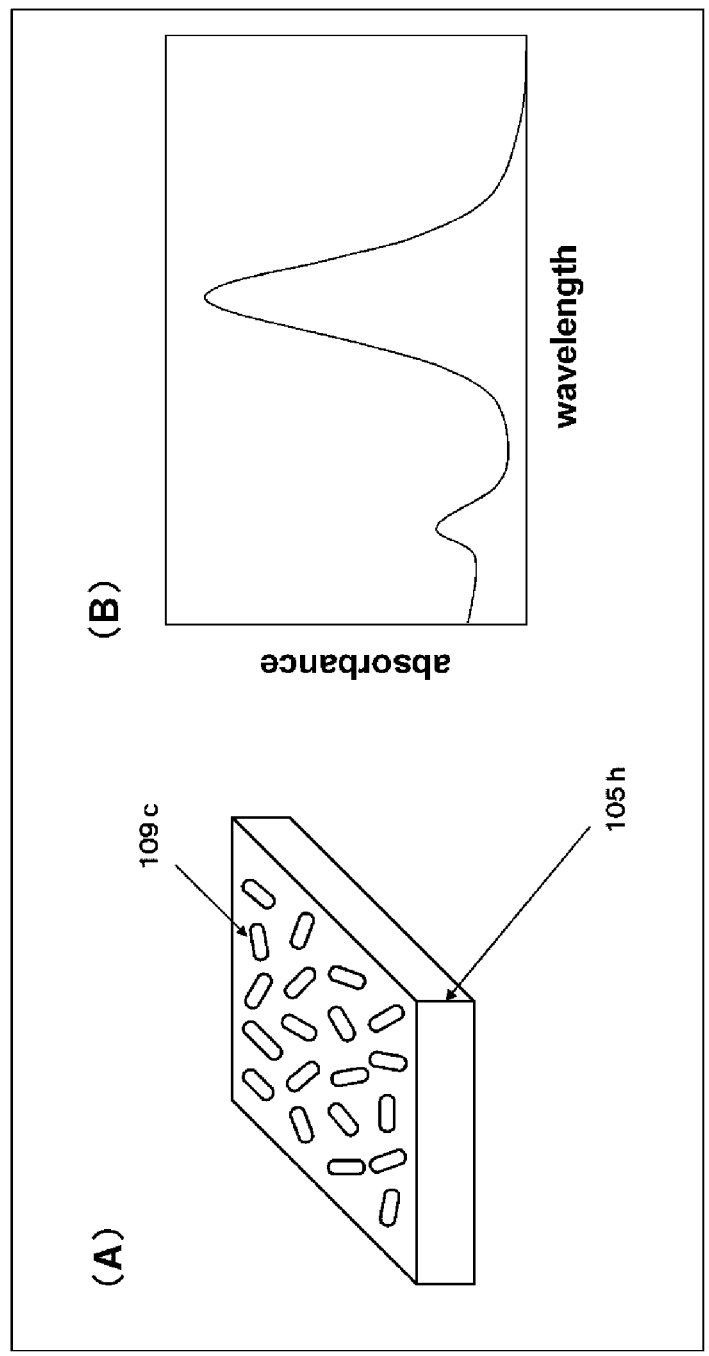
FIG. 5(A) is a configuration diagram of a substrate 105h on which randomly-aligned Au nanorods are formed.
FIG. 5(B) is a graph showing an absorption spectrum of the substrate 105h on which the randomly-aligned Au nanorods are formed.

The substrates comprising the plurality of first metallic nanorods 109a and the second metallic nanorods 109b having the long axes that are aligned in the same direction have strong polarization properties. FIG. 5(A) illustrates a substrate 105h comprising randomly-aligned metallic nanorods 109c. FIG. 5(B) shows its absorption spectrum. The substrate 105h has absorption peaks in localized surface plasmon resonance bands originating from the short axis and the long axis, with respect to any incident polarized light, as shown in FIG. 5(B).

Figure 6:
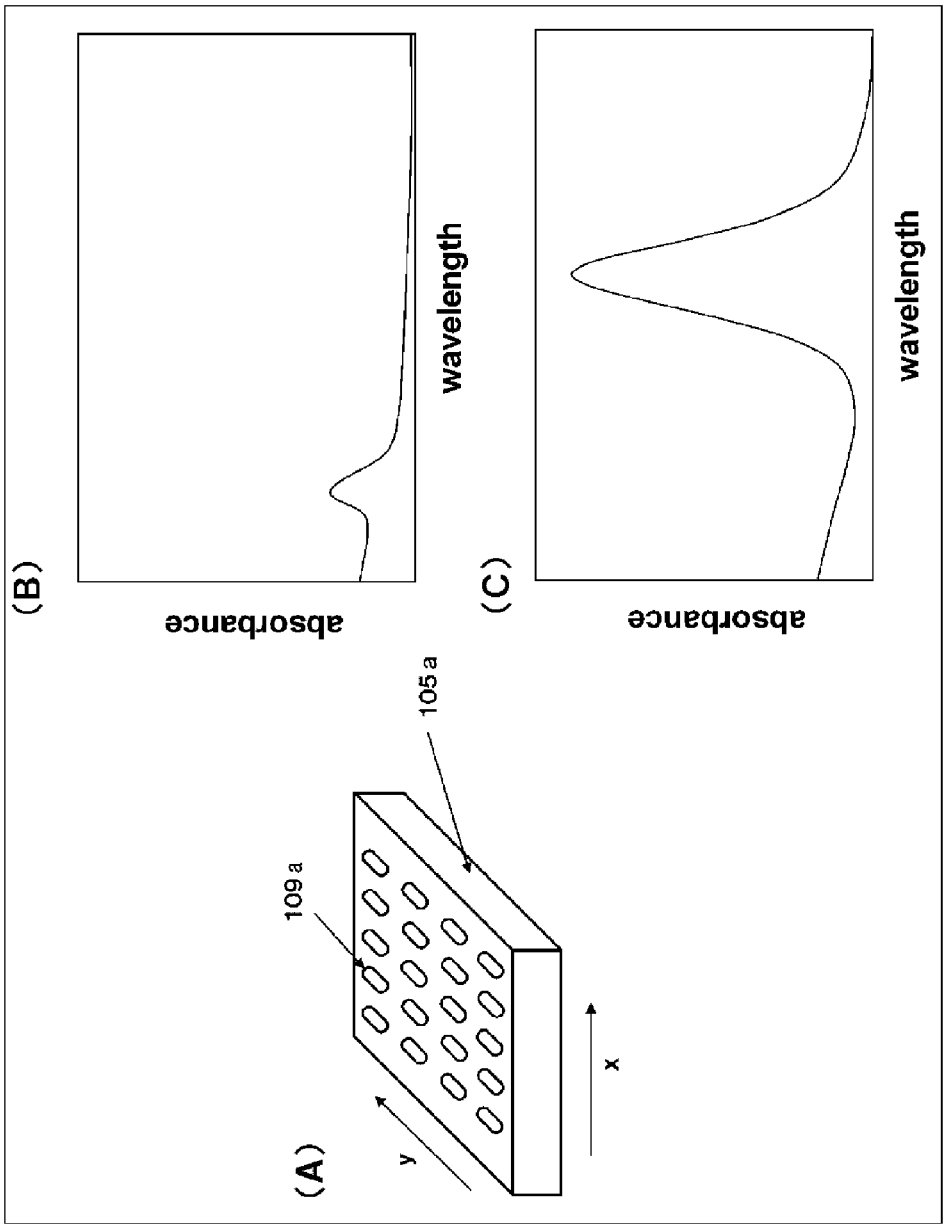
FIG. 6(A) is a configuration diagram of a substrate 105a on which Au nanorods are formed such that the long axes thereof are aligned in the same direction.
FIG. 6(B) is a graph showing an absorption spectrum of the substrate 105a when polarized light having the short-axis direction of the Au nanorods is applied thereto.
FIG. 6(C) shows an absorption spectrum of the substrate 105a when the polarized light having the long-axis direction of the Au nanorods is applied thereto.

FIG. 6(A) illustrates the substrate 105a comprising the first metallic nanorods 109a having the long axes that are aligned in the same direction y. FIG. 6(B) shows an absorption spectrum that occurs by applying polarized light along a direction perpendicular to the long axes (i.e., an x direction in FIG. 6(A)). FIG. 6(C) shows an absorption spectrum that occurs by applying polarized light along a direction parallel to the long axes (the y direction in FIG. 6(A)).

As understood from FIGS. 6(B) and 6(C), the substrate 105a exhibits only an absorption spectrum by the localized surface plasmon resonance band originating from the short axis, with respect to the polarized light along the x direction. The substrate 105a exhibits only an absorption spectrum by the localized surface plasmon resonance band originating from the long axis, with respect to the polarized light along the y direction.

By setting polarized light to be parallel to either of the long axes of the first metallic nanorods 109a or the long axes of the second metallic nanorods 109b, an absorption spectrum specific to either one of the first substrate 105a or the second substrate 105b is allowed to be obtained. Either one of the polarizing plate 103 or the cell 105 is rotated about the optical axis such that the polarized light becomes parallel to either of the long axes of the first metallic nanorods 109a or the long axes of the second metallic nanorods 109b. Both the polarizing plate 103 and the cell 105 can be rotated.

The long axes of the plurality of first metallic nanorods need to be orthogonal to the long axes of the plurality of second metallic nanorods. The reason will be described below with reference to FIG. 20.

FIG. 20(A) illustrates an exploded diagram of the cell 105. On the first substrate 105a of the cell 105, the first metallic nanorods 109a are formed such that the long axes thereof are aligned in the same direction. An axis parallel to the long axes of the first metallic nanorods 109a is defined as a y direction, and an axis parallel to the short axes of the first metallic nanorods 109a is defined as an x direction. On the second substrate 105b of the cell 105, the second metallic nanorods 109b are formed such that the long axes thereof are aligned in the same direction. As shown in FIG. 20(A), the second metallic nanorods 109b are formed such that the long axes thereof are inclined at an angle of 45 degrees relative to the y direction. In other words, in the cell 105, the long axes of the plurality of first metallic nanorods 109a are not orthogonal to the long axes of the plurality of second metallic nanorods 109b.

In the cell 105, in order to obtain only absorption by the localized surface plasmon resonance originating from the long axes of the first metallic nanorods 109a on the first substrate 105a, polarized light parallel to the long axes of the first metallic nanorods 109a, namely, polarized light having the y direction, needs to be incident thereon. FIG. 20(B) shows an absorption spectrum of the first substrate 105a when polarized light having the y direction is applied to the cell 105. According to FIG. 20(B), only the absorption peak by the localized surface plasmon resonance originating from the long axes of the first metallic nanorods 109a is allowed to be observed.

The polarized light having the y direction and applied to the cell 105 passes through the first substrate 105a and then is applied to the second substrate 105b. FIG. 20(C) shows an absorption spectrum of the second substrate 105b when the polarized light having the y direction is applied thereto. According to FIG. 20(C), it is seen that two absorption peaks appear. The absorption peak on the long wavelength side is the absorption peak by the localized surface plasmon resonance originating from the long axes of the second metallic nanorods 109b, and the absorption peak on the short wavelength side is the absorption peak by the localized surface plasmon resonance originating from the short axes of the second metallic nanorods 109b. The reason why the two absorption peaks appear is that the polarized light having the y direction is composed of two polarized light components parallel to the long axes and the short axes, respectively, of the second metallic nanorods 109b. Thus, with the polarized light having the y direction that is applied in order to obtain only the absorption by the localized surface plasmon resonance originating from the long axes of the first metallic nanorods 109a, absorption by the localized surface plasmon resonance originating from the long axes of the second metallic nanorods 109b is also obtained. Thus, it is impossible to obtain only the absorption by the localized surface plasmon resonance originating from the long axes of the first metallic nanorods 109a. Therefore, when the polarized light having the y direction is applied in order to obtain only the absorption by the localized surface plasmon resonance originating from the long axes of the first metallic nanorods 109a, it is necessary to prevent occurrence of the absorption by the localized surface plasmon resonance originating from the long axes of the second metallic nanorods 109b. In order to do this, the long axes of the second metallic nanorods 109b need to be perpendicular to the polarized light having the y direction.

(Method for Measuring Concentration of Antigen)

Hereinafter, a method for measuring the concentration of an antigen contained in a test solution by using the apparatus 100 according to Embodiment 1 will be described with reference to the drawings.

(Pre-measurement)

First, the apparatus 100 is prepared. Then, the cell 105 is inserted into the optical measuring apparatus 200. In pre-measurement, the cell 105 does not retain a test solution. In other words, in general, the cell 105 is in a vacuum state or filled with air.

The light source 101 is powered on. The light radiated from the light source 101 is adjusted by the lenses 102 and passes through the polarizing plate 103.

The polarized light which has passed through the polarizing plate 103 has only a polarized light component parallel to the long axes of the first metallic nanorods 109a. When the polarized light passes through the cell 105, the intensity attenuation light reaches maximum at the localized surface plasmon resonant wavelength originating from the long axes of the first metallic nanorods 109a. The light does not attenuate at the localized surface plasmon resonant wavelength originating from the long axes of the second metallic nanorods 109b. The polarized light having passed through the cell 105 is converged by the lenses 104, passes through the slit 106, is dispersed by the grating device 107, and reaches the photoreceiver 108. This polarized light corresponds to "third light" in CLAIMS.

The microcomputer 110 determines the wavelength at which the light attenuation is maximum, on the basis of the light intensity detected at each photo-receptive region of the photoreceiver 108. This wavelength is stored in the memory 111 as a wavelength $$\lambda a0 \qquad [\text{Chem.04}]$$

before supplying a test solution.
After the wavelength $$\lambda a0 \qquad [\text{Chem.05}]$$

is determined, the microcomputer 110 rotates the polarizing plate 103 by 90 degrees. This rotation causes the polarized light which has passed through the polarizing plate 103 to have only a polarized light component parallel to the long axes of the second metallic nanorods 109b.

When the polarized light passes through the cell 105, the light attenuation reaches maximum at the localized surface plasmon resonant wavelength originating from the long axes of the second metallic nanorods 109b. This polarized light corresponds to "fourth light" in CLAIMS. The light does not attenuate at the localized surface plasmon resonant wavelength originating from the long axes of the first metallic nanorods 109a. Similarly to the above, the wavelength is stored in the memory 111 as $$\text{a wavelength } \lambda b0 \qquad [\text{Chem.06}]$$

before supplying a test solution.

$$\text{Wavelength } \lambda a0: \qquad [\text{Chem.07}]$$

the wavelength at which the light attenuation is maximized which occurs by the polarized light, which has only the polarized light component parallel to the long axes of the first metallic nanorods 109a, passing through the cell 105 before supplying a test solution.

$$\text{Wavelength } \lambda b0: \qquad [\text{Chem.08}]$$

the wavelength at which the light attenuation is maximized which occurs by the polarized light, which has only the polarized light component parallel to the long axes of the second metallic nanorods 109b, passing through the cell 105 before supplying a test solution.

In the present embodiment, before supplying a test solution, $$\text{the wavelength } \lambda a0 \text{ and the wavelength } \lambda b0 \qquad [\text{Chem.09}]$$

are determined by the cell 105 and the apparatus 100. Alternatively, previously determined $$\text{wavelength } \lambda a0 \text{ and wavelength } \lambda b0 \qquad [\text{Chem.10}]$$

may be stored in the memory 111.

(Step (a) and step (b))

The apparatus 100 is prepared. The cell 105 is filled with a test solution. An antigen contained in the test solution bonds specifically to the antibody 112a on the first metallic nanorods 109a. Meanwhile, the antigen does not bond to the blocking substance 112c.

(Step (c))

After the antigen sufficiently bonds to the antibody 112a, the light source 101 is powered on. Similarly to the measurement of $$\text{the wavelength } \lambda a0, \qquad [\text{Chem.11}]$$

the polarized light having only the polarized light component parallel to the long axes of the first metallic nanorods 109a is transmitted through the cell 105 to obtain first light. The photoreceiver 108 receives the first light.

(Step (d))

The microcomputer 110 determines the wavelength at which the light attenuation is maximum, on the basis of the light intensity at the photoreceiver 108. This wavelength is stored in the memory 111 as $$\text{a wavelength } \lambda a1 \qquad [\text{Chem.12}]$$

after supplying the test solution. Then, the microcomputer 110 calculates the shift amount $$\Delta \lambda a \qquad [\text{Chem.13}]$$

of the resonant wavelength caused by the bonding of the antigen to the antibody, from the following equation:

$$\Delta \lambda a = \lambda a1 - \lambda a0 \qquad [\text{Chem.14}]$$

(Step (e))

Thereafter, the microcomputer 110 rotates the polarizing plate 103 by 90 degrees. This rotation causes the polarized light which has passed through the polarizing plate 103 to have only the polarized light component parallel to the long axes of the second metallic nanorods 109b.

(Step (f))

Similarly to the measurement of $$\text{the wavelength } \lambda b0, \qquad [\text{Chem.15}]$$

the polarized light having only the polarized light component parallel to the long axes of the second metallic nanorods 109b is transmitted through the cell 105 to obtain second light. The photoreceiver 108 receives the second light.

(Step (g))

The microcomputer 110 determines the wavelength at which the light attenuation is maximum, on the basis of the light intensity at the photoreceiver 108. This wavelength is stored in the memory 111 as a wavelength $$\lambda b1 \qquad [\text{Chem.16}]$$

after supplying the test solution. Then, the microcomputer 110 calculates the shift amount $$\Delta \lambda b \qquad [\text{Chem.17}]$$

of the resonant wavelength caused by the contact of the test solution with the plurality of second metallic nanorods 109*b*, from the following equation:

$$\Delta\lambda b = \lambda b1 - \lambda b0 \quad \text{[Chem.18]}$$

(Step (h))

The microcomputer 110 calculates the difference between $$\Delta\lambda a \text{ and } \Delta\lambda b \quad \text{[Chem.19]}$$

to calculate an accurate shift amount $$\Delta\lambda \quad \text{[Chem.20]}$$

of the resonant wavelength caused by the bonding of the antigen to the antibody 112*a*.

Thereafter, the microcomputer 110 calculates the concentration of the antigen with reference to the correlation between the accurate resonant wavelength shift amount $$\Delta\lambda \quad \text{[Chem.21]}$$

and a concentration of the antigen (hereinafter, referred to as a "calibration curve"). Needless to say, the microcomputer 110 previously stores the calibration curve in the memory 111.

The calculated concentration of the antigen is notified to a user, for example, with a speaker (not shown) or a display.

The calibration curve can be obtained, for example, according to the following procedure.

Test solutions having various antigen concentrations are produced. The solvent of the test solutions is pure water, and the solute of the test solutions is an antigen. The localized surface plasmon resonant $$\text{wavelengths } \lambda a0 \text{ and } \lambda b0 \quad \text{[Chem.22]}$$

of the cell 105 before supplying a test solution are measured. Then, a test solution having a known antigen concentration is supplied to the cell 105, and $$\text{the wavelengths } \lambda a1 \text{ and } \lambda b1 \quad \text{[Chem.23]}$$

are measured. Then, a resonant wavelength shift amount $$\Delta\lambda \quad \text{[Chem.24]}$$

with respect to an antigen concentration is calculated from the following three equations.

$$\Delta\lambda a = \lambda a1 - \lambda a0$$

$$\Delta\lambda b = \lambda b1 - \lambda b0$$

$$\Delta\lambda = \Delta\lambda a - \Delta\lambda b \quad \text{[Chem.25]}$$

For the test solutions having the various antigen concentrations, $$\Delta\lambda \quad \text{[Chem.26]}$$

is obtained and plotted with a vertical axis representing the resonant wavelength shift amount $$\Delta\lambda \quad \text{[Chem.27]}$$

and a horizontal axis representing the antigen concentration, whereby the calibration curve is obtained.

Details of Object and Advantageous Effect of the Present Invention

The localized surface plasmon resonant wavelength originating from the long axis is very sensitive to the refractive index near each metallic nanorod.

When Au nanorods each having an average short axis length of 10 nm and an average long axis length of 37 m are used, a change in refractive index of $1.0*10^0$ causes the localized surface plasmon resonant wavelength originating from the long axis to shift to the long wavelength side by about 220 nm.

The antigen bonds to the antibody with which the Au nanorods are modified, and the localized surface plasmon resonant wavelength shifts due to a change in the refractive index near each Au nanorod.

The difference between the localized surface plasmon resonant wavelength before the antigen bonds to the antibody and the localized surface plasmon resonant wavelength after the antigen bonds to the antibody, namely, the resonant wavelength shift amount, is measured. On the basis of the resonant wavelength shift amount, the amount of a refractive index change caused by the bonding of the antigen to the antibody is calculated. In this manner, the concentration of the antigen is calculated.

However, the refractive index near each metallic nanorod changes due to not only the bonding of the antigen to the antibody but also the medium near the metallic nanorod being changed from the vacuum or air to the test solution.

In other words, the resonant wavelength shift amount $$\Delta\lambda a \quad \text{[Chem.28]}$$

includes the amount of shift of the localized surface plasmon resonant wavelength caused by the bonding of the antigen to the antibody (hereinafter, referred to as "shift amount A1". This is equal to $$\Delta\lambda) \quad \text{[Chem.29]}$$

and the amount of shift of the resonant wavelength caused by the medium near each metallic nanorod being changed from the vacuum or air to the test solution (hereinafter, referred to as "shift amount A2").

The test solution may contain albumin and globulin. Each individual has a different albumin concentration. Each individual has a different globulin concentration. The shift amount $$\Delta\lambda a. \quad \text{[Chem.30]}$$

includes an albumin concentration and a globulin concentration as the shift amount A2. Thus, it is difficult to accurately obtain the concentration of the antigen only from the shift amount $$\Delta\lambda a. \quad \text{[Chem.31]}$$

The reason will be described in detail with reference to FIGS. 18 to 23.

FIG. 18(A) illustrates the first substrate 105*a* having the first metallic nanorods 109*a* modified with the first antibody 112*a*.

FIG. 18(B) shows an absorption spectrum that occurs by light parallel to the long axes of the first metallic nanorods 109*a*, being applied to the first substrate 105*a* before a test solution is supplied.

$$\lambda a0 \quad \text{[Chem.32]}$$

is the obtained localized surface plasmon resonant wavelength.

FIG. 18(C) shows an absorption spectrum after a test solution is supplied and the antigen sufficiently bonds to the first antibody 112*a*.

$$\lambda a1 \quad \text{[Chem.33]}$$

is the localized surface plasmon resonant wavelength in the spectrum indicated by the solid line in FIG. 18(C). The dotted line in FIG. 18(C) indicates the absorption spectrum in FIG. 18(B).

The amount $$\Delta\lambda a \quad [\text{Chem.34}]$$

of shift of the resonant wavelength caused by the bonding of the antigen to the antibody 112a is represented by the following equation:

$$\Delta\lambda a = \lambda a1 - \lambda a0 \quad [\text{Chem.35}]$$

$$\Delta\lambda a \quad [\text{Chem.36}]$$

includes not only the shift amount A1 and but also the shift amount A2.

When the concentration of the antigen is 0 M, $$\Delta\lambda a [\text{Chem.37}]$$

indicates only the resonant wavelength shift (shift amount A2) caused by the refractive index change that occurs by the medium near each metallic nanorod being changed from the air to the test solution.

The refractive index of the test solution changes depending on the concentrations of materials (e.g., albumin and globulin) other than the antigen. The concentrations of albumin and globulin can change depending on each individual. Therefore, even when the concentration of the antigen is 0 M, $$\Delta\lambda a [\text{Chem.38}]$$

can change depending on each individual. Thus, the concentration of the antigen cannot accurately be calculated only from $$\Delta\lambda a [\text{Chem.39}]$$

Particularly, when the concentration of the antigen is equal to or lower than $10^{-10}$ M, this tendency appears prominently. This is because blood concentrations of albumin and globulin are about $10^{-3}$.

When the test substance is a disease marker or hormone contained in body fluid such as blood, urine, saliva, and perspiration, the present invention is particularly effective. The reason will be described below.

The concentration of an antigen contained in body fluid is very low. More particularly, the concentration is $10^{-15}$ to $10^{-8}$ M. Meanwhile, the concentration of albumin or globulin contained in blood is about $10^{-3}$ M. Each individual has a different concentration of albumin or globulin. The maximum concentration is about double the minimum concentration. For example, the difference between the maximum concentration and the minimum concentration of albumin is about 2000 mg/dl.

This concentration difference causes a difference in refractive index of blood between individuals. A protein concentration change of 1 mg/dl causes a refractive index change of about $1.9 *10^{-6}$. Therefore, the maximum difference in refractive index by albumin between individuals is about $3.8*10^{-3}$.

When Au nanorods are used, a refractive index change of $1.0*10^{0}$ (=1) causes a resonant wavelength shift of about 250 nm. Therefore, a refractive index change of $3.8*10^{-3}$ causes a resonant wavelength shift of about 0.95 nm. Meanwhile, the shift amount of the resonant wavelength caused by causing the antigen having a concentration of about $10^{-12}$ M to bond to the antibody is about $10^{-2}$ nm. Thus, the shift amount of the resonant wavelength caused by causing the antigen to bond to the antibody is much lower than the shift amount caused by the albumin concentration difference that depends on each individual. Further, in blood, sugar and salt influence the refractive index.

Thus, the shift amount of the resonant wavelength cannot be identified as the shift amount caused depending on the individual or as the shift amount caused by causing the antigen to bond to the antibody, and hence the antigen concentration cannot accurately be obtained.

In the present invention, as shown in FIG. 19(A), the second substrate 105b comprises, as a reference region, the plurality of second metallic nanorods 109b that are modified with the blocking substance 112c.

FIG. 19(B) shows an absorption spectrum that occurs by light parallel to the long axes of the second metallic nanorods 109b, being applied to the second substrate 105b before a test solution is supplied.

$$\lambda b0 \quad [\text{Chem.40}]$$

is the obtained localized surface plasmon resonant wavelength.

FIG. 19(C) shows an absorption spectrum after a test solution is supplied.

$$\lambda b1 \quad [\text{Chem.41}]$$

is the localized surface plasmon resonant wavelength in the spectrum indicated by the solid line in FIG. 19(C). The dotted line in FIG. 19(C) indicates the absorption spectrum in FIG. 19(B).

The resonant wavelength shift amount $$\Delta\lambda b \quad [\text{Chem.42}]$$

is equal to the shift amount A2 of the resonant wavelength caused by the medium near the plurality of second metallic nanorods 109b being changed from the vacuum or air to the test solution, and is represented by the following equation:

$$\Delta\lambda b = \lambda b1 - \lambda b0 \quad [\text{Chem.43}]$$

The resonant wavelength shift amount $$A1 (=\Delta\lambda) \quad [\text{Chem.44}]$$

is calculated by obtaining the difference between $$\Delta\lambda a \text{ and } \Delta\lambda b.$$

(Others)

In the present embodiment, the halogen light source 101 is used as a light source. However, any light source can be used without particularly limiting the light source, as long as it radiates light including the localized surface plasmon resonant wavelength. In the present embodiment, the halogen light source 101 of which light is unpolarized is used. However, a light source having particular polarized light can be used. An example of the light source having particular polarized light is a laser light source. When the light source having particular polarized light is used, a wavelength plate can be used as polarized light control means.

Means for rotating the polarization direction by rotating the light source having particular polarized light with a motor can also be used as polarized light control means.

At that time, it is preferred to include a sensor for determining whether or not a test solution is filled. For example, electrodes are provided to the cover glass 105e and the first substrate 105a, and, further, other electrodes are provided to the first substrate 105a and the second substrate 105b. After the cell 105 is inserted into the optical measuring apparatus 200, a weak voltage is applied to the electrodes. In a case where the test solution is, for example, blood, when the test solution is filled, an electric current flows between the electrodes due to the electrolytes contained in the blood. Thus, it is determined whether or not the test solution is filled in the first test solution retention space 105f and the second test solution retention space 105g. Further, it is preferred to automatically power on the halogen light source 101 by using output of the sensor, since the measurement is allowed to be automated.

(Embodiment 2)

Another embodiment of the present invention will be described with reference to FIGS. 7 to 9.

Figure 7:
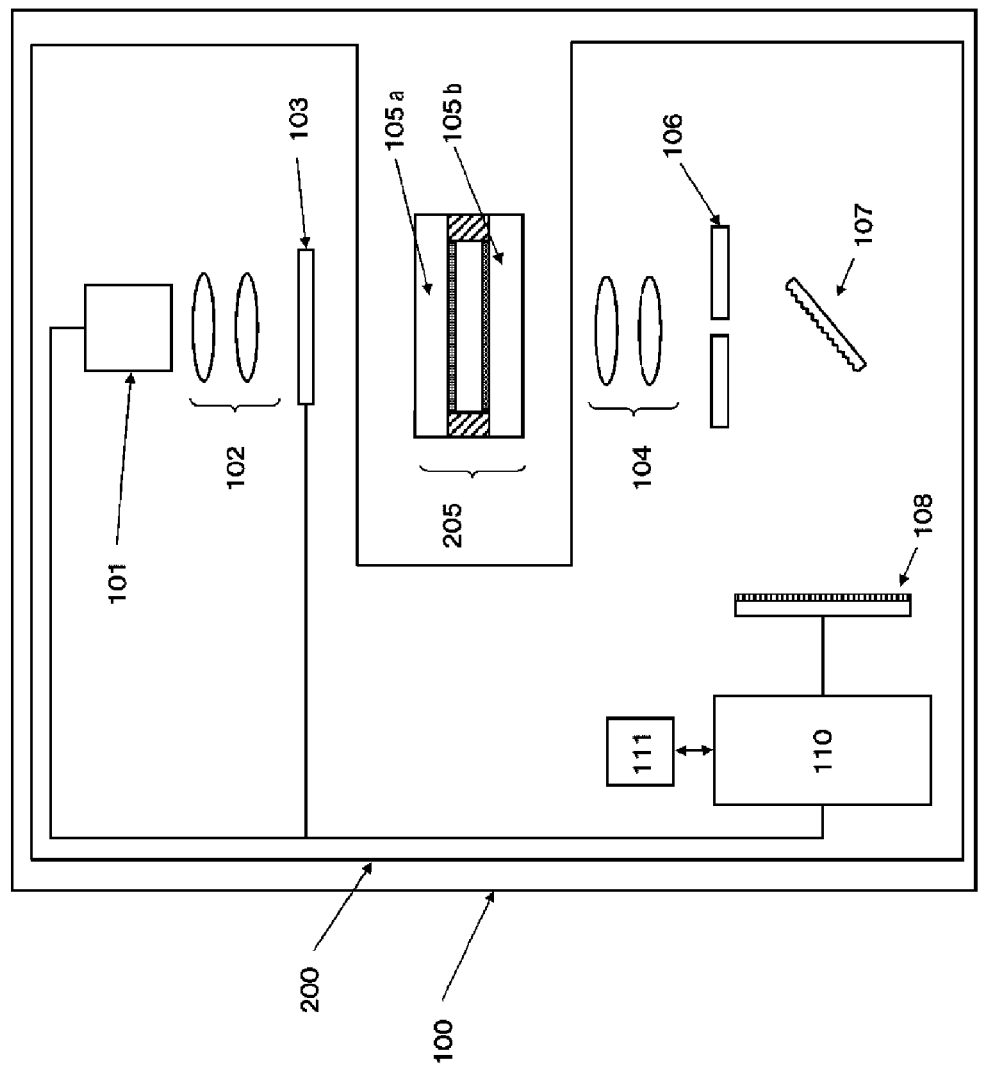
FIG. 7 is a diagram illustrating a configuration of a biogenic substance concentration measuring apparatus according to Embodiment 2 of the present invention.
Figure 8:
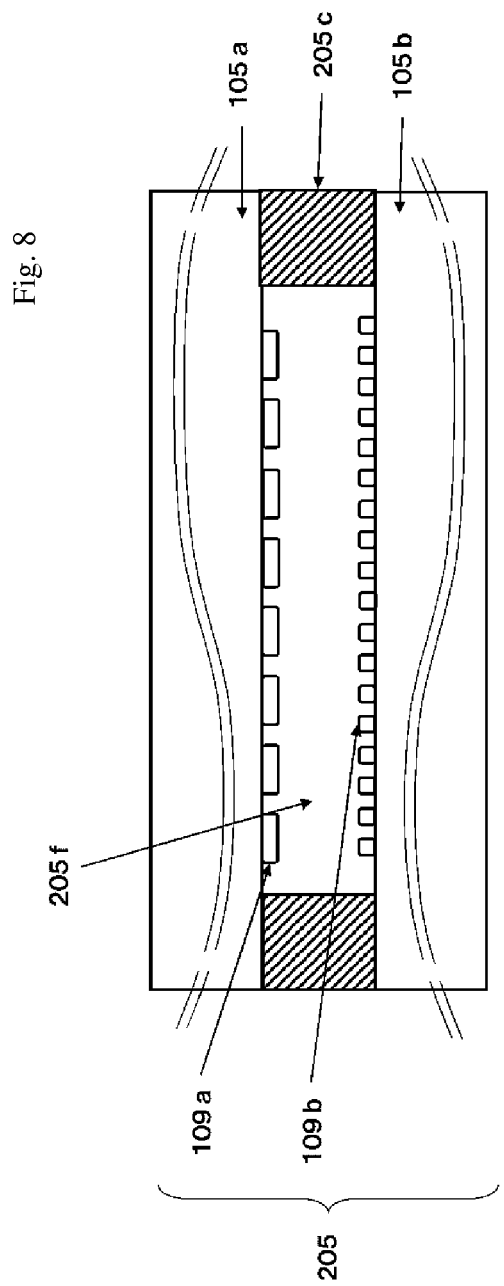
FIG. 8 is a diagram illustrating a cross section of a cell 205 according to Embodiment 2 of the present invention.
Figure 9:
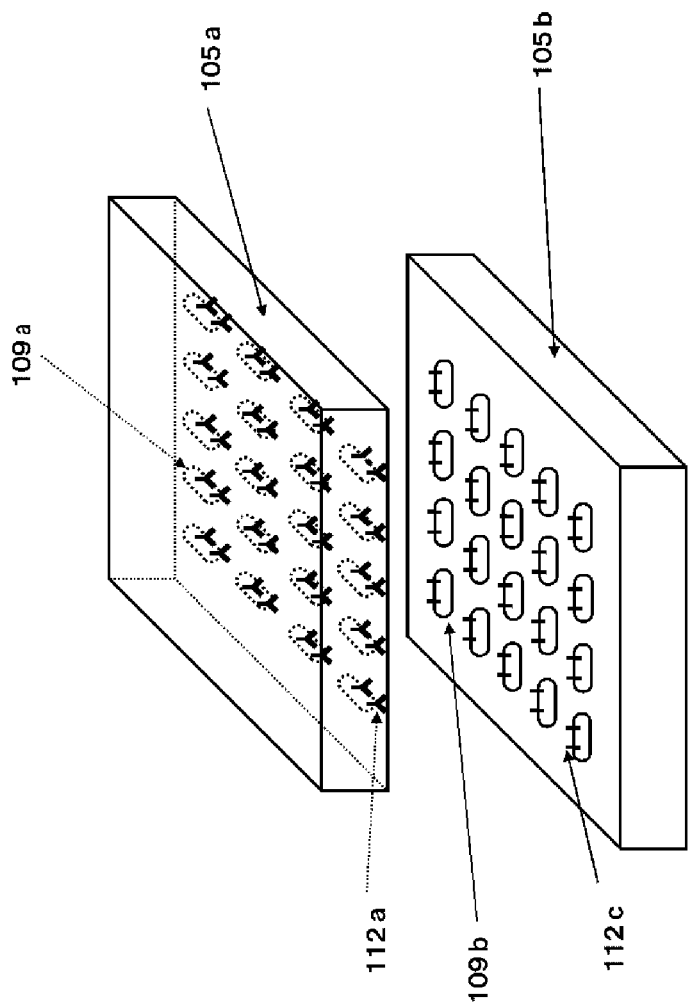
FIG. 9 is a perspective view of a part of the cell 205 according to Embodiment 2 of the present invention.

In FIGS. 7 to 9, the same components as those in FIGS. 1 to 3 are designated by the same reference numerals, and the description thereof is omitted.

FIG. 7 is a diagram illustrating a configuration of a biogenic substance concentration measuring apparatus according to Embodiment 2 of the present invention. In FIG. 7, the configuration differs from that in Embodiment 1 in that a cell 205 is configured as a cell for biogenic substance concentration measurement such that the surface of the first substrate 105a on which the first metallic nanorods 109a are formed faces the surface of the second substrate 105b on which the second metallic nanorods 109b are formed. The other configuration is the same, and thus the description thereof is omitted.

FIG. 8 is a cross-sectional view of the cell 205 according to Embodiment 2 of the present invention. The cell 205 is composed of the first substrate 105a and the second substrate 105b on which the first metallic nanorods 109a and the second metallic nanorods 109b are provided, and a spacer 205c. In addition, the cell 205 is further composed of a test solution retention space 205f formed by the first substrate 105a, the spacer 205c, and the second substrate 105b, a supply inlet and a drain outlet (not shown) for a test solution.

FIG. 9 is a perspective view of parts of the first substrate 105a and the second substrate 105b of the cell 205 where the metallic nanorods are formed. On the first substrate 105a, the metallic nanorods 109a are formed such that the long axes thereof are aligned in the same direction. On the second substrate 105b, the second metallic nanorods 109b are formed such that the long axes thereof are aligned perpendicularly to the long axes of the first metallic nanorods 109a formed on the first substrate 105a. The first metallic nanorods 109a are modified with the antibody 112a. The second metallic nanorods 109b are modified with the blocking substance 112c.

The cell 205 is formed such that the surfaces on which the first metallic nanorods 109a and the second metallic nanorods 109b face each other. Unlike Embodiment 1, the number of the test solution retention space is one, and thus it is easy to supply a test solution.

A sensor for determining whether or not a test solution is filled has a simple configuration. For example, electrodes are provided to the first substrate 105a and the second substrate 105b. After the cell 205 is inserted into the optical measuring apparatus 200, a weak voltage is applied to the electrodes. In the case where the test solution is, for example, blood, when the test solution is filled, an electric current flows between the electrodes due to the electrolytes contained in the blood. Thus, it is determined whether or not the test solution is filled in the test solution retention space 205f. Further, it is preferred to automatically power on the halogen light source 101 by using output of the sensor, since the measurement is allowed to be automated.

The operation of the biogenic substance concentration measuring apparatus according to the present embodiment is the same as that in Embodiment 1, and thus the description thereof is omitted. According to the present embodiment, a cell for biogenic substance concentration measurement is allowed to be provided which makes it easy to supply a test solution and which is easily fabricated.

(Embodiment 3)

Figure 10:
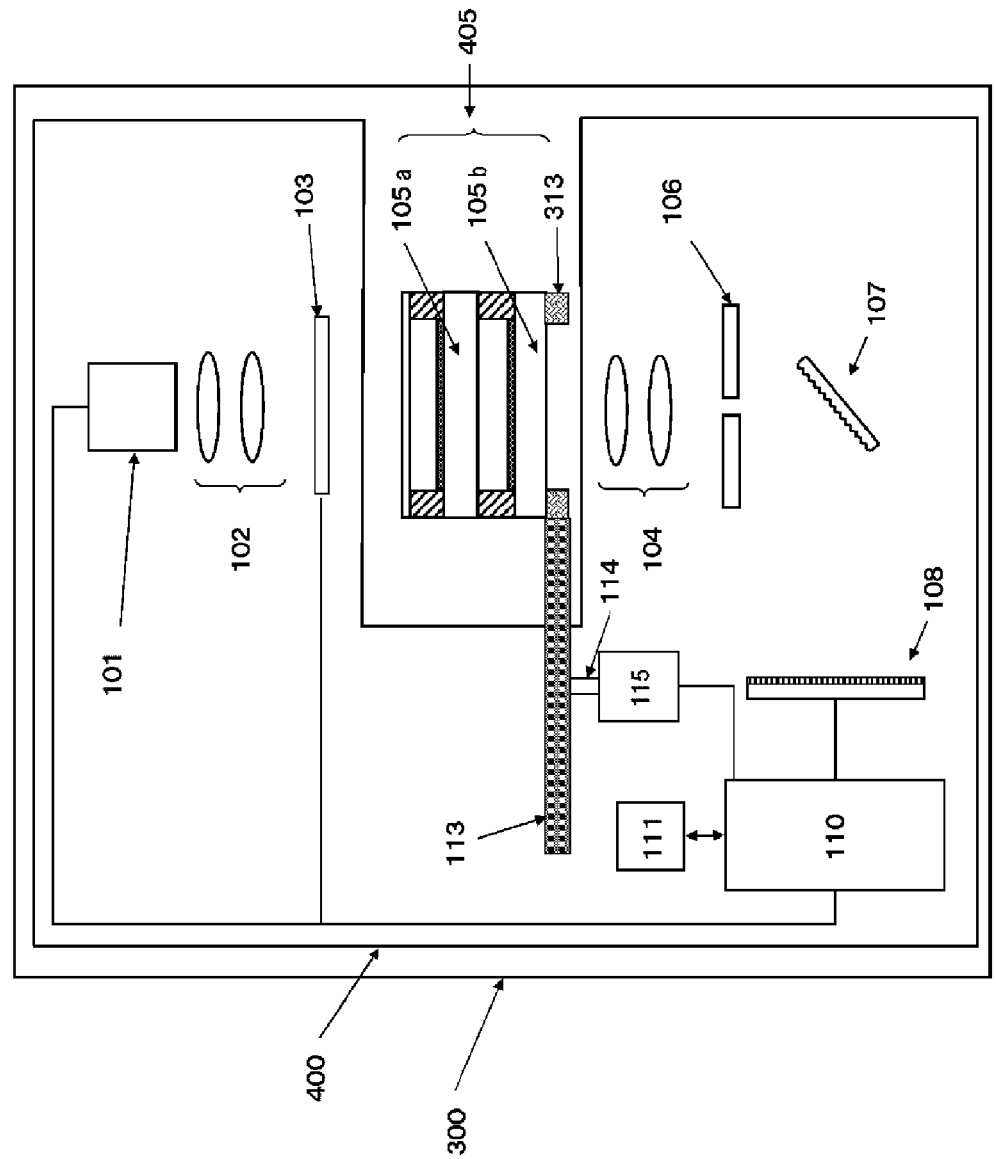
FIG. 10 is a diagram illustrating a configuration of a biogenic substance concentration measuring apparatus according to Embodiment 3 of the present invention.

Another embodiment of the present invention will be described with reference to FIGS. 10 and 11.

The configuration in the present embodiment differs from that in Embodiment 1 in that a cell 405 for biogenic substance concentration measurement comprises a cog-wheel 313 at the bottom of the second substrate 105b, and an optical measuring apparatus 400 comprises a cog-wheel 113 coupled to the cog-wheel 313 of the cell 405 for biogenic substance concentration measurement, a shaft 114 coupled to the cog-wheel 113, and a motor 115, coupled to the shaft 114, for rotating the cog-wheel 113. The other configuration is the same, and thus the description thereof is omitted.

Figure 11:
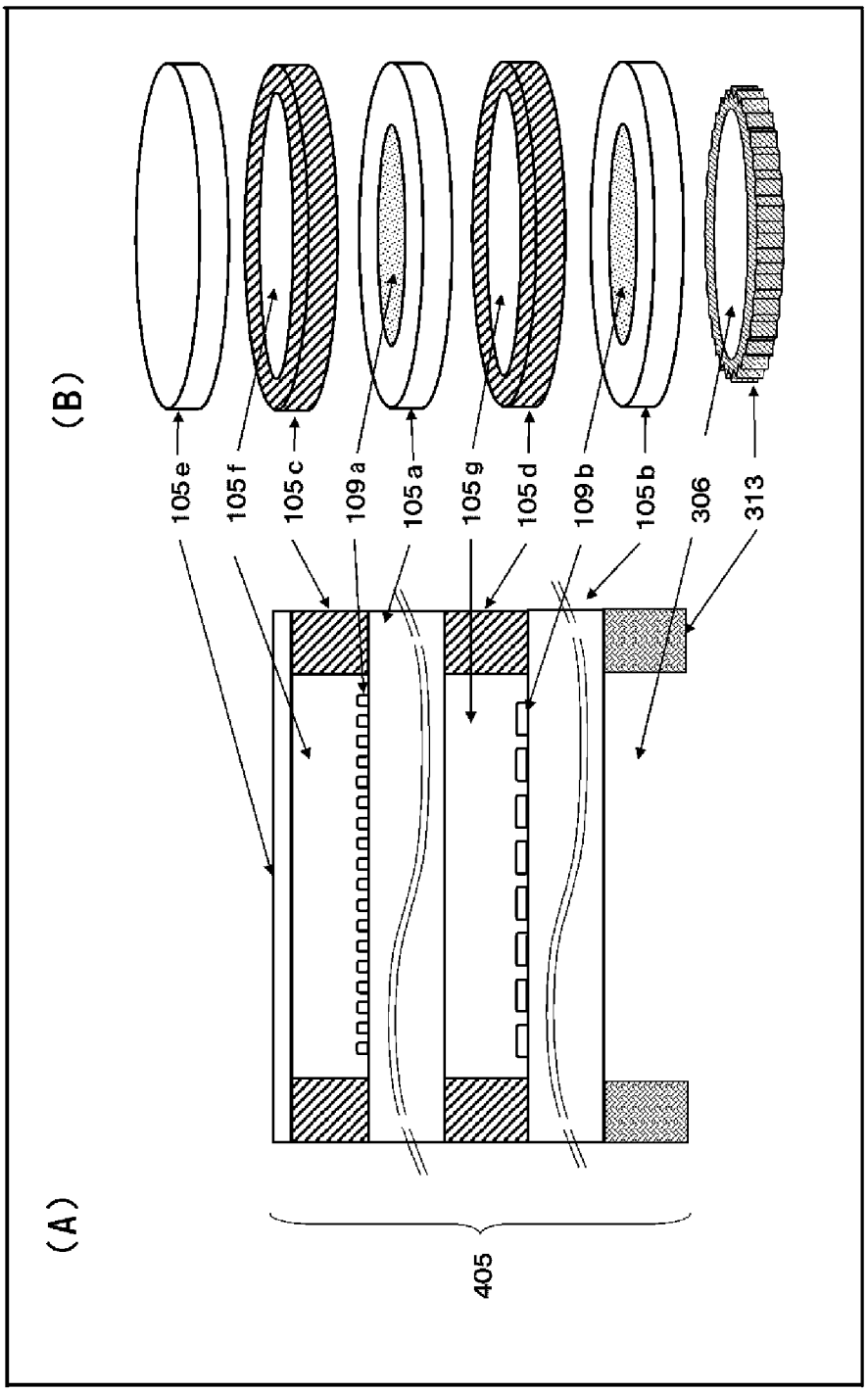
FIG. 11 is a diagram illustrating a configuration of a cell 405 for biogenic substance concentration measurement according to Embodiment 3 of the present invention.

FIG. 11 is a diagram illustrating a configuration of the cell 405 for biogenic substance concentration measurement according to Embodiment 3 of the present invention. FIG. 11A is a diagram illustrating a cross section of the cell 405 for biogenic substance concentration measurement, and FIG. 11B is an exploded perspective view of the cell 405 for biogenic substance concentration measurement.

The cog-wheel 313 is provided at the bottom of the second substrate 105b. The cog-wheel 313 has a through-hole 306 in order not to block light that has passed through the first substrate 105a and the second substrate 105b.

The cog-wheel 113, the shaft 114, the motor 115, and the cog-wheel 313 in the present embodiment correspond to cell rotation means in the present invention. In the present embodiment, the polarizing plate 103 is used for selecting the polarized light from the halogen light source 101. However, a light source having particular polarized light can also be used. An example of the light source having particular polarized light is a laser light source. When the light source having particular polarized light is used, it is unnecessary to use the polarizing plate 103.

Next, the operation of the biogenic substance concentration measuring apparatus according to the present embodiment will be described with reference to the drawings. First, the cell 405 is inserted into the optical measuring apparatus 400. When the cell 405 is inserted into the optical measuring apparatus 400, the halogen light source 101 is powered on. The light radiated by the halogen light source 101 is adjusted by the lenses 102 and passes through the polarizing plate 103.

The microcomputer 110 rotates the cog-wheel 113 by using the motor 115 to rotate the cell 405, such that the polarization direction of the light which has passed through the polarizing plate 103 and the long-axis direction of the first metallic nanorods 109a formed on the first substrate 105a are parallel to each other.

As means for detecting that the polarization direction of the light which has passed through the polarizing plate 103 and the long-axis direction of the first metallic nanorods 109a formed on the first substrate 105a are parallel to each other, a method may be used in which a recess (not shown) is provided in the cell 405 for allowing the long-axis direction of the first metallic nanorods 109a formed on the first substrate 105a to be recognized, and is detected with a photosensor.

The light which has passed through the polarizing plate 103 passes through the cell 405 that has been rotated such that the light is parallel to the long axes of the first metallic nanorods 109a formed on the first substrate 105a. At that time, the light attenuation reaches maximum at the localized surface plasmon resonant wavelength originating from the long axes of the first metallic nanorods 109a formed on the first substrate 105a. The light does not attenuate at the localized surface plasmon resonant wavelength originating from the long axes of the second metallic nanorods 109b formed on the second substrate 105b. The light which has passed through the cell 105 is converged by the lenses 104, passes through the slit 106, is dispersed by the grating device 107, and reaches each photo-receptive region of the photoreceiver 108.

The microcomputer 110 determines the wavelength at which the light attenuation is maximum, on the basis of the light intensity detected at each photo-receptive region of the photoreceiver 108, and stores the determined wavelength in the memory 111 as a first wavelength $$\lambda a0 \qquad [\text{Chem.46}]$$

before test solution supply.
After determining the first wavelength $$\lambda a0 \qquad [\text{Chem.47}]$$

before test solution supply, the microcomputer 110 rotates the cog-wheel 113 by using the motor 115 to rotate the cell 405, such that the polarization direction of the light having passed through the polarizing plate 103 and the long-axis direction of the second metallic nanorods 109b formed on the second substrate 105b are parallel to each other.

The light which has passed through the polarizing plate 103 passes through the cell 405 that has been rotated such that the light is parallel to the long axes of the second metallic nanorods 109b formed on the second substrate 105b. At that time, the light does not attenuate at the localized surface plasmon resonant wavelength originating from the long axes of the first metallic nanorods 109a formed on the first substrate 105a. Meanwhile, at the same time, the light attenuation reaches maximum at the localized surface plasmon resonant wavelength originating from the long axes of the second metallic nanorods 109b formed on the second substrate 105b.

The light which has passed through the cell 105 is converged by the lenses 104, passes through the slit 106, is dispersed by the grating device 107, and reaches each photo-receptive region of the photoreceiver 108. The microcomputer 110 determines the wavelength at which the light attenuation is maximum, on the basis of the light intensity detected at each photo-receptive region of the photoreceiver 108, stores the determined wavelength in the memory 111 as a second wavelength $$\lambda b0 \qquad [\text{Chem.48}]$$

before test solution supply, and powers off the halogen light source 101. A state where the measurement of $$\lambda a0 \text{ and } \lambda b0 \qquad [\text{Chem.49}]$$

is completed and a test solution can be supplied is notified to the user, for example, by being notified with a sound through a speaker (not shown) or being displayed on a display (not shown). Then, a test solution containing the test substance is supplied.

When the test solution is filled in the cell 105, the antigen that is the test substance in the test solution bonds specifically to the antibody 112a on the first metallic nanorods 109a.

After a predetermined time period elapses and the antigen bonds to the antibody 112a, the halogen light source 101 is powered on. The light radiated by the halogen light source 101 is adjusted by the lenses 102 and passes through the polarizing plate 103.

The microcomputer 110 rotates the cog-wheel 113 by using the motor 115 to rotate the cell 405, such that the polarization direction of the light which has passed through the polarizing plate 103 and the long-axis direction of the first metallic nanorods 109a formed on the first substrate 105a are parallel to each other.

The light which has passed through the polarizing plate 103 passes through the cell 405 that has been rotated such that the light is parallel to the long axes of the first metallic nanorods 109a formed on the first substrate 105a. At that time, the light attenuation reaches maximum at the localized surface plasmon resonant wavelength originating from the long axes of the first metallic nanorods 109a formed on the first substrate 105a. The light does not attenuate at the localized surface plasmon resonant wavelength originating from the long axes of the second metallic nanorods 109b formed on the second substrate 105b.

The light having passed through the cell 105 is converged by the lenses 104, passes through the slit 106, is dispersed by the grating device 107, and reaches each photo-receptive region of the photoreceiver 108.

The microcomputer 110 determines the wavelength at which the light attenuation is maximum, on the basis of the light intensity detected at each photo-receptive region of the photoreceiver 108, and stores the determined wavelength in the memory 111 as a first wavelength $$\lambda a1 \qquad [\text{Chem.50}]$$

after the test solution is supplied.

At that time, it is preferred to include a sensor for determining whether or not a test solution is filled. For example, electrodes are provided to the cover glass 105e and the first substrate 105a, and, further, other electrodes are provided to the first substrate 105a and the second substrate 105b. After the cell 405 is inserted into the optical measuring apparatus 400, a weak voltage is applied to the electrodes. In the case where the test solution is, for example, blood, when the test solution is filled, an electric current flows between the electrodes due to the electrolytes contained in the blood. Thus, it is determined whether or not the test solution is filled in the test solution retention space 105f and the second test solution retention space 105g. Further, it is preferred to automatically power on the halogen light source 101 by using output of the sensor, since the measurement is allowed to be automated.

After determining the first wavelength $$\lambda a1 \qquad [\text{Chem.51}]$$

after the test solution is supplied, the microcomputer 110 rotates the cog-wheel 113 by using the motor 115 to rotate the cell 405, such that the polarization direction of the light having passed through the polarizing plate 103 and the long-axis direction of the second metallic nanorods 109b formed on the second substrate 105b are parallel to each other.

The light which has passed through the polarizing plate 103 passes through the cell 405 that has been rotated such that the light is parallel to the long axes of the second metallic nanorods 109b formed on the second substrate 105b. At that time, the light does not attenuate at the localized surface plasmon resonant wavelength originating from the long axes of the first metallic nanorods 109a formed on the first substrate 105a. Meanwhile, at the same time, the light attenuation reaches maximum at the localized surface plasmon resonant wavelength originating from the long axes of the second metallic nanorods 109b formed on the second substrate 105b.

The light which has passed through the cell 105 is converged by the lenses 104, passes through the slit 106, is dispersed by the grating device 107, and reaches each photo-receptive region of the photoreceiver 108. The microcomputer 110 determines the wavelength at which the light attenuation is maximum, on the basis of the light intensity detected at each photo-receptive region of the photoreceiver 108, and stores the determined wavelength in the memory 111 as a second wavelength $$\lambda b1 \qquad [\text{Chem.52}]$$

after the test solution is supplied.

Next, the microcomputer 110 calculates the difference between $$\lambda a1 \text{ and } \lambda a0 \qquad [\text{Chem.53}]$$

to calculate the resonant wavelength shift amount $$\Delta \lambda a \qquad [\text{Chem.54}]$$

in the first substrate.

Similarly, the microcomputer 110 calculates the difference between $$\lambda b1 \text{ and } \lambda b0 \qquad [\text{Chem.55}]$$

to calculate the resonant wavelength shift amount $$\Delta \lambda b \qquad [\text{Chem.56}]$$

in the second substrate.

Further, the microcomputer 110 calculates the difference between $$\Delta \lambda a \text{ and } \Delta \lambda b \qquad [\text{Chem.57}]$$

to calculate the resonant wavelength shift amount $$\Delta \lambda \qquad [\text{Chem.58}]$$

caused by the antigen, which is the test substance, bonding to the antibody 112a.

Thereafter, the microcomputer 110 refers to the correlation between the resonant wavelength shift amount $$\Delta \lambda \qquad [\text{Chem.59}]$$

and the test substance concentration which correlation is previously stored in the memory 111, and calculates the concentration of the test substance. The calculated concentration of the test substance is notified to the user, for example, by being notified with a sound through a speaker (not shown) or being displayed on a display (not shown).

In the present embodiment, the cell rotation means is provided in the biogenic substance concentration measuring apparatus according to Embodiment 1. However, the cell rotation means may similarly be provided in the biogenic substance concentration measuring apparatus according to Embodiment 2. In the present embodiment, the modified substance is the antibody, but another substance can be the antibody. In the present embodiment, the halogen light source 101 is used as a light source. However, any light source can be used without particularly limiting the light source, as long as it radiates light including the localized surface plasmon resonant wavelength.

According to the present embodiment, the cell is merely rotated, and it is unnecessary to change the positional relation among the light source, the detection region, and the photodetector and to move the measurement region. It is unnecessary to provide a plurality of optical axes for light irradiation and to increase the size of the irradiated region, and thus the apparatus configuration is simple and a biogenic substance concentration is allowed to be measured with high accuracy.

(Embodiment 4)

Another embodiment of the present invention will be described with reference to FIGS. 12 to 14.

Figure 12:
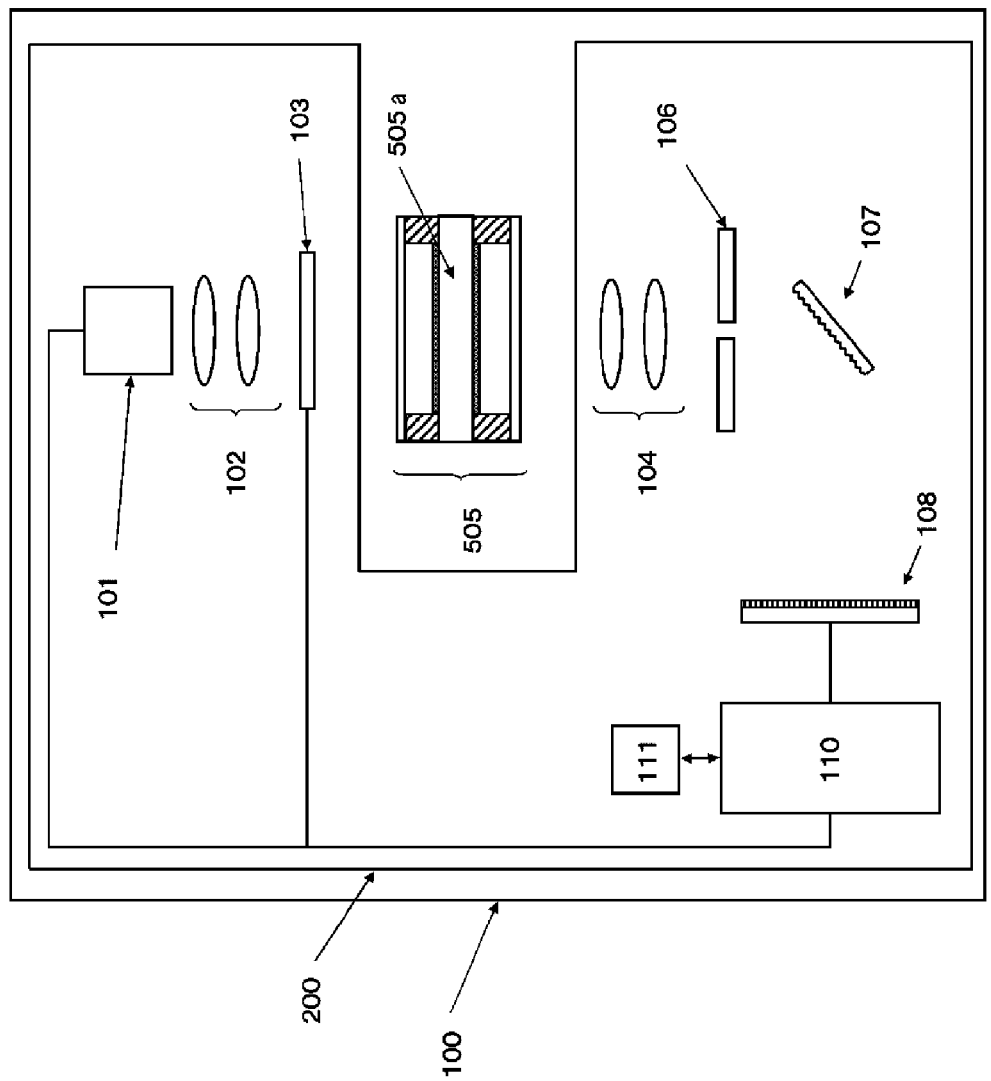
FIG. 12 is a diagram illustrating a configuration of a biogenic substance concentration measuring apparatus according to Embodiment 4 of the present invention.

In FIG. 12, the configuration differs from that in Embodiment 1 in that a cell 505 that is a cell for biogenic substance concentration measurement is configured such that the second metallic nanorods 109b are formed on the surface of a planar substrate 505a that is on the back of the surface of the planar substrate 505a on which the first metallic nanorods 109a are formed. The configuration other than the cell 505 is the same, and thus the description thereof is omitted.

Figure 13:
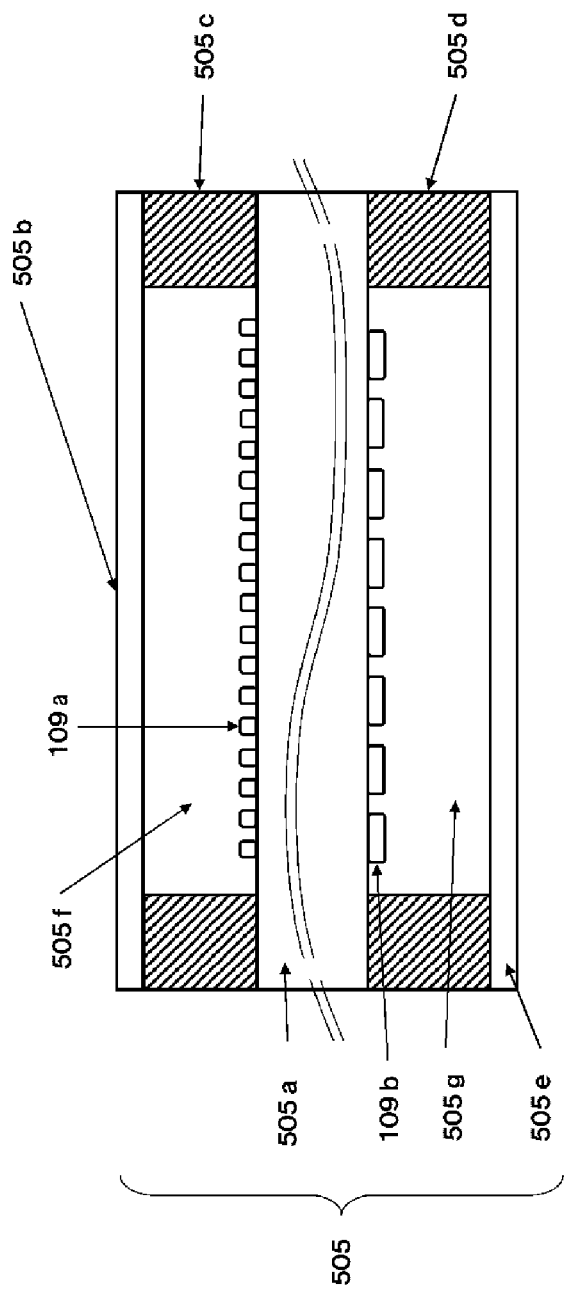
FIG. 13 is a diagram illustrating a cross section of a cell 505 according to Embodiment 4 of the present invention.

FIG. 13 is a cross-sectional view of the cell 505 according to Embodiment 4. The cell 505 is composed of the planar substrate 505a on which the first metallic nanorods 109a and the second metallic nanorods 109b are provided, a first cover glass 505b, a second cover glass 505e, a first spacer 505c, a second spacer 505d, and a supply inlet (not shown) and a drain outlet (not shown) for a test solution. In addition, the cell 505 has a first test solution retention space 505f formed by the first cover glass 505b, the planar substrate 505a, and the first spacer 505c, and a second test solution retention space 505g formed by the second cover glass 505e, the planar substrate 505a, and the second spacer 505d.

Figure 14:
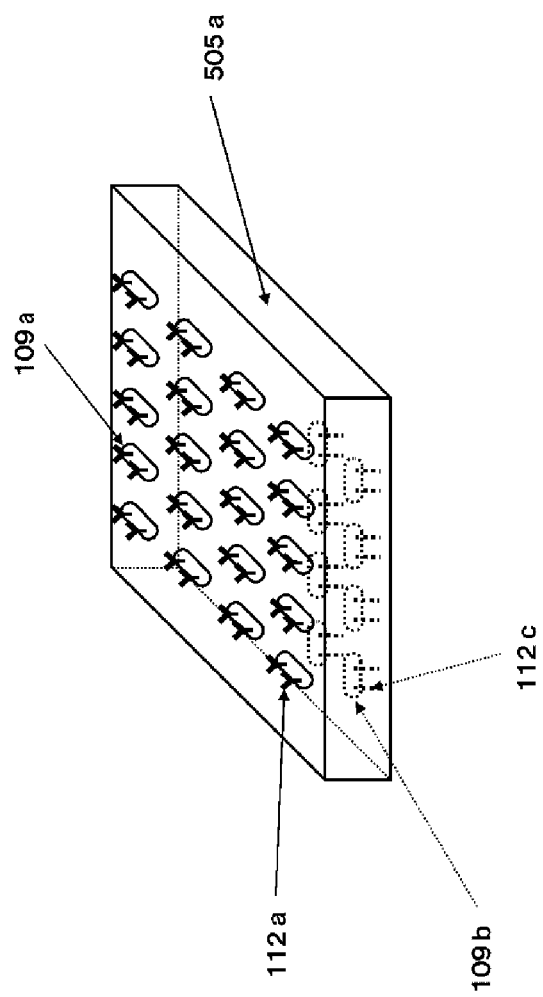
FIG. 14 is a perspective view of a part of the cell 505 according to Embodiment 4 of the present invention.

FIG. 14 is a perspective view of a part of the planar substrate 505a of the cell 505 where the metallic nanorods are formed. On one surface of the planar substrate 505a, the first metallic nanorods 109a are formed such that the long axes thereof are aligned in the same direction. On the other surface of the planar substrate 505a, the second metallic nanorods 109b (only partially shown) are formed such that the long axes thereof are aligned perpendicularly to the long-axis direction of the first metallic nanorods 109a. The first metallic nanorods 109a are modified with the first antibody 112a, and the second metallic nanorods 109b are modified with the blocking substance 112c.

Due to such a configuration, a substrate on which metallic nanorods are formed does not need to be attached, and thus the relation between the directions of the long axes of the first metallic nanorods 109a and the second metallic nanorods 109b is not changed from perpendicularity by the attaching. Thus, this leads to improvement of measurement accuracy. The operation of the biogenic substance concentration measuring apparatus according to the present embodiment is the same as that in Embodiment 1, and thus the description thereof is omitted. Further, a measurement region and a reference region may be provided as in Embodiment 3.

According to the present embodiment, a cell for biogenic substance concentration measurement is allowed to be provided which is produced with high accuracy and which provides high measurement accuracy.

(Embodiment 5)

Another embodiment of the present invention will be described with reference to FIGS. 15 to 17.

Figure 15:
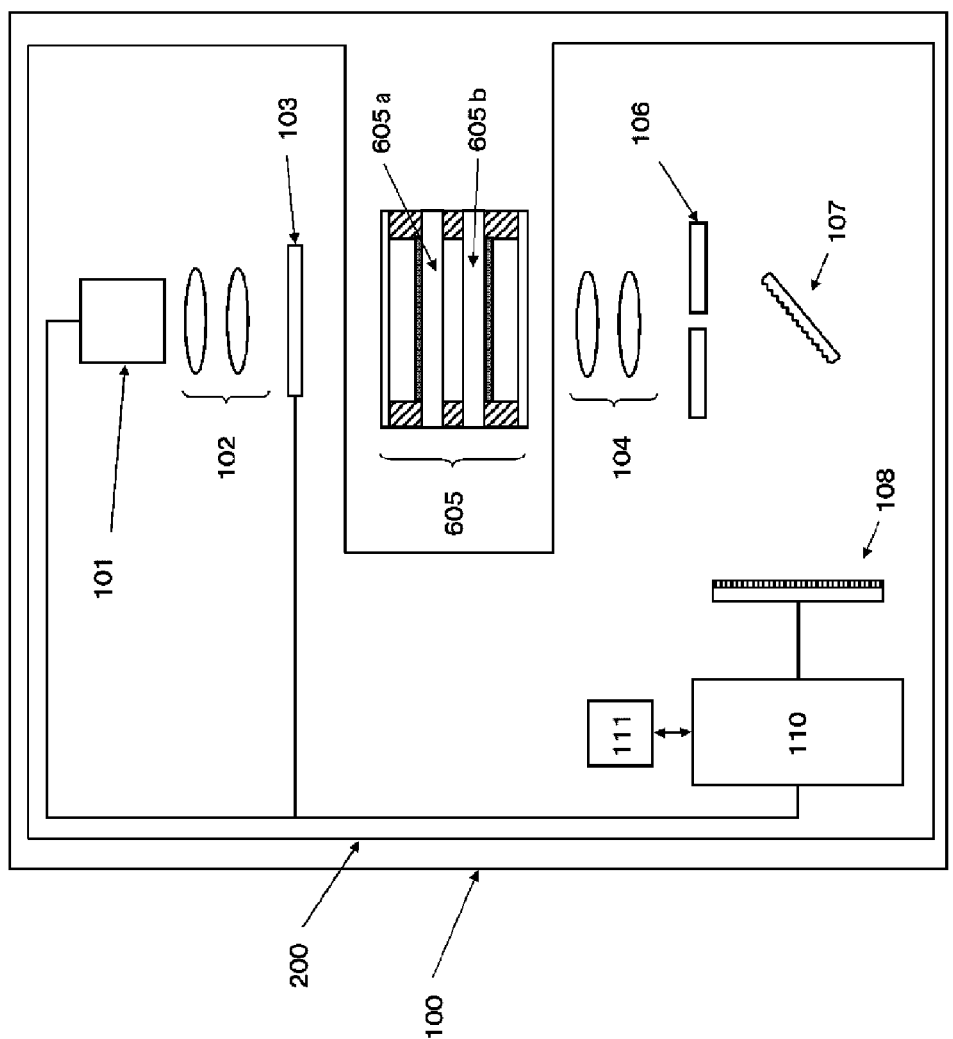
FIG. 15 is a diagram illustrating a configuration of a biogenic substance concentration measuring apparatus according to Embodiment 5 of the present invention.

In FIG. 15, the configuration differs from that in Embodiment 1 in that a cell 605 that is a cell for biogenic substance concentration measurement is configured such that the surface of a first substrate 605a on which the first metallic nanorods 109a are formed and the surface of a second substrate 605b on which the second metallic nanorods 109b are formed face in the opposite directions. The configuration other than the cell 605 is the same, and thus the description thereof is omitted.

Figure 16:
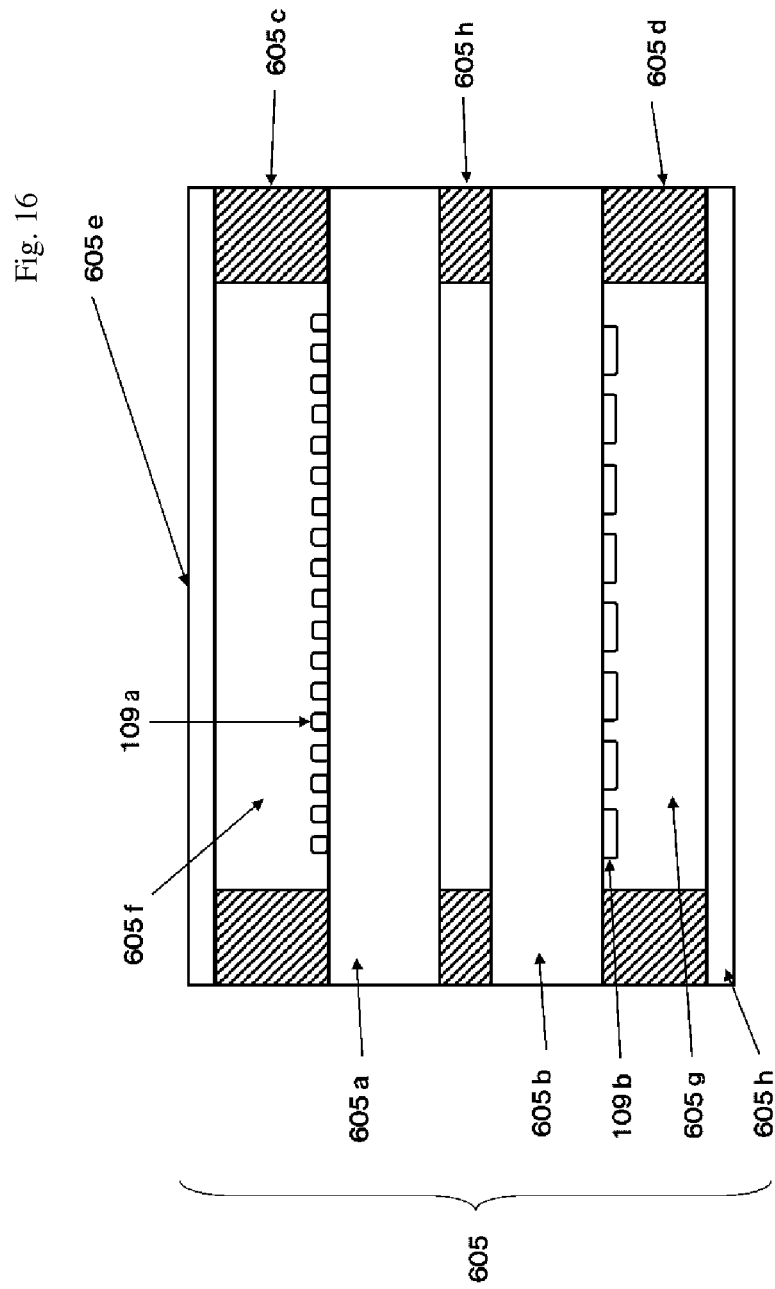
FIG. 16 is a diagram illustrating a cross section of a cell 605 according to Embodiment 5 of the present invention.

FIG. 16 is a cross-sectional view of the cell 605 according to Embodiment 5. The cell 605 is composed of the first substrate 605a on which the first metallic nanorods 109a are provided, the second substrate 605b on which the second metallic nanorods 109b are provided, a first cover glass 605e, a second cover glass 605h, a first spacer 605c, a second spacer 605d, a third spacer 605i, and a supply inlet (not shown) and a drain outlet (not shown) for a test solution. In addition, the cell 605 has a first test solution retention space 605f formed by the first cover glass 605e, the first substrate 605a, and the first spacer 605c, and a second test solution retention space 605g formed by the second cover glass 605h, the second substrate 605b, and the third spacer 605i.

Figure 17:
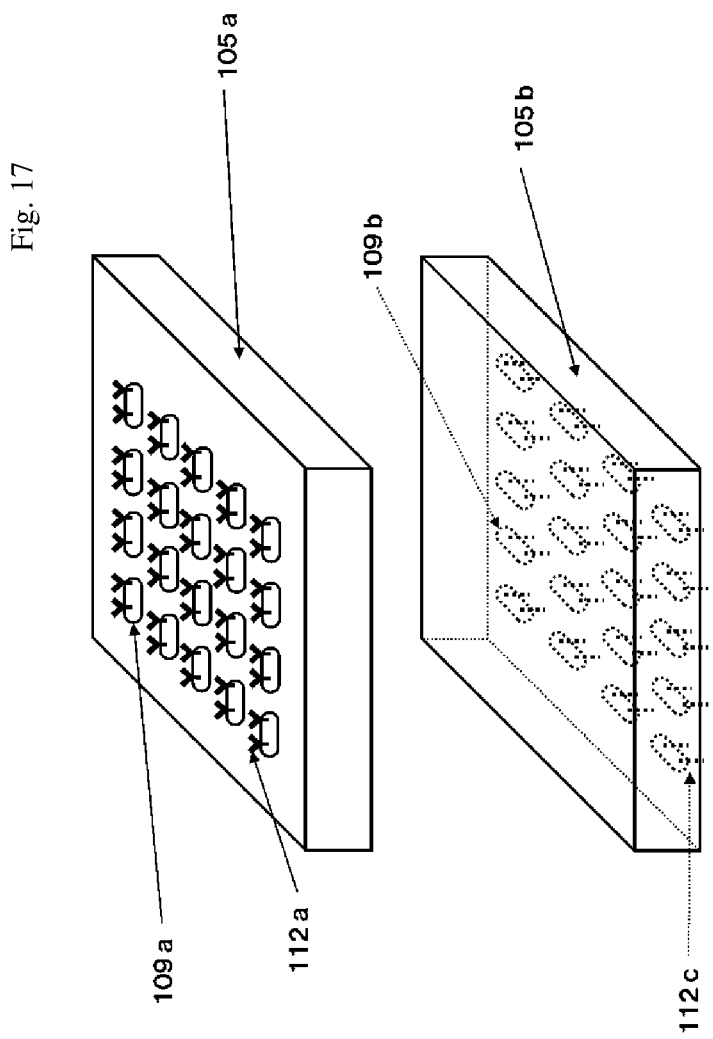
FIG. 17 is a perspective view of a part of the cell 605 according to Embodiment 5 of the present invention.
Figure 18:
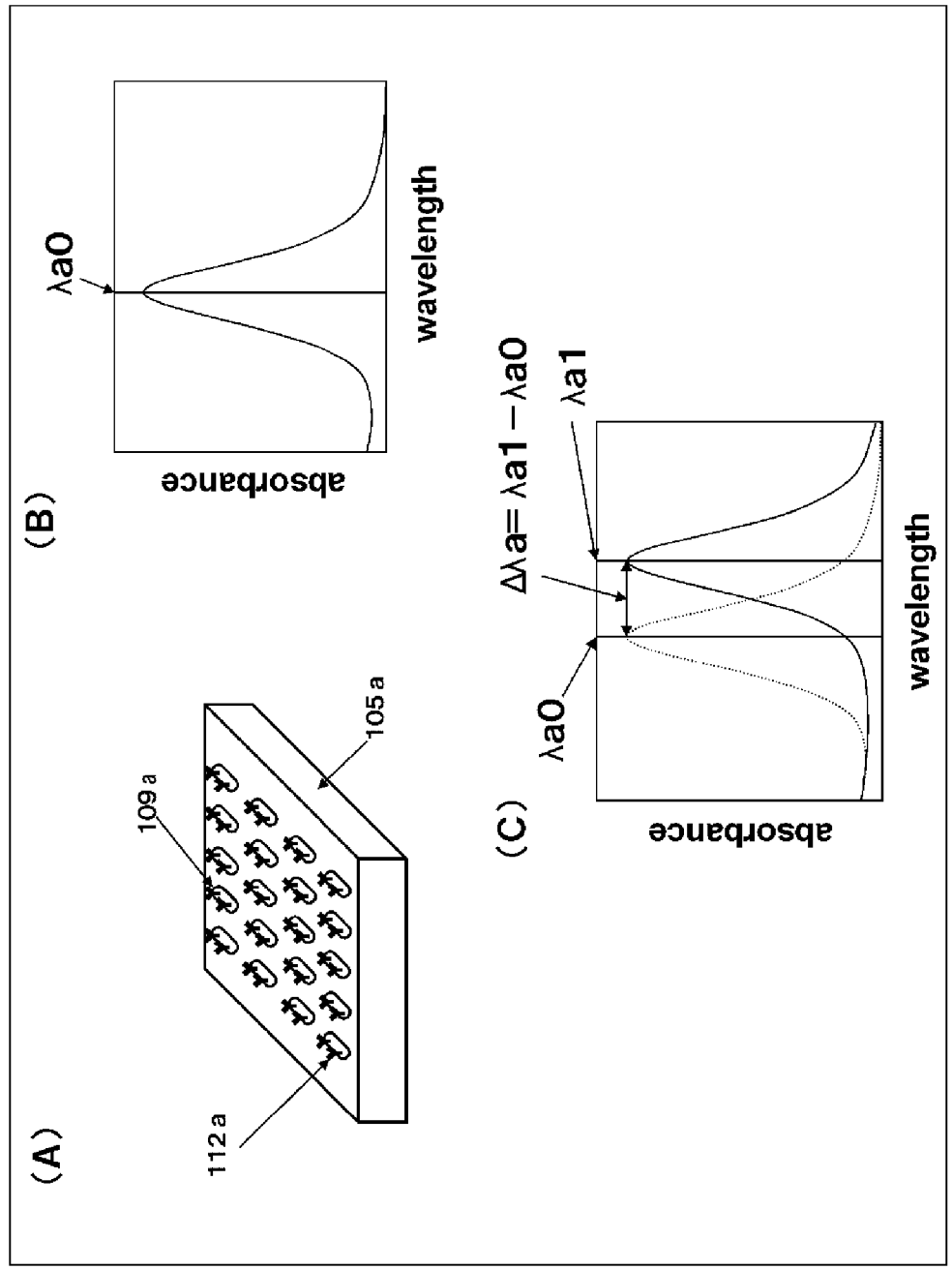
FIG. 18(A) is a configuration diagram of the first substrate 105a on which Au nanorods are formed such that the long axes thereof are aligned in the same direction.
FIG. 18(B) is a graph showing an absorption spectrum of the first substrate 105a when polarized light parallel to the long axes of the Au nanorods before test solution supply is applied thereto.
FIG. 18(C) is a graph showing an absorption spectrum of the first substrate 105a when the polarized light parallel to the long axes of the Au nanorods after test solution supply is applied thereto.
Figure 19:
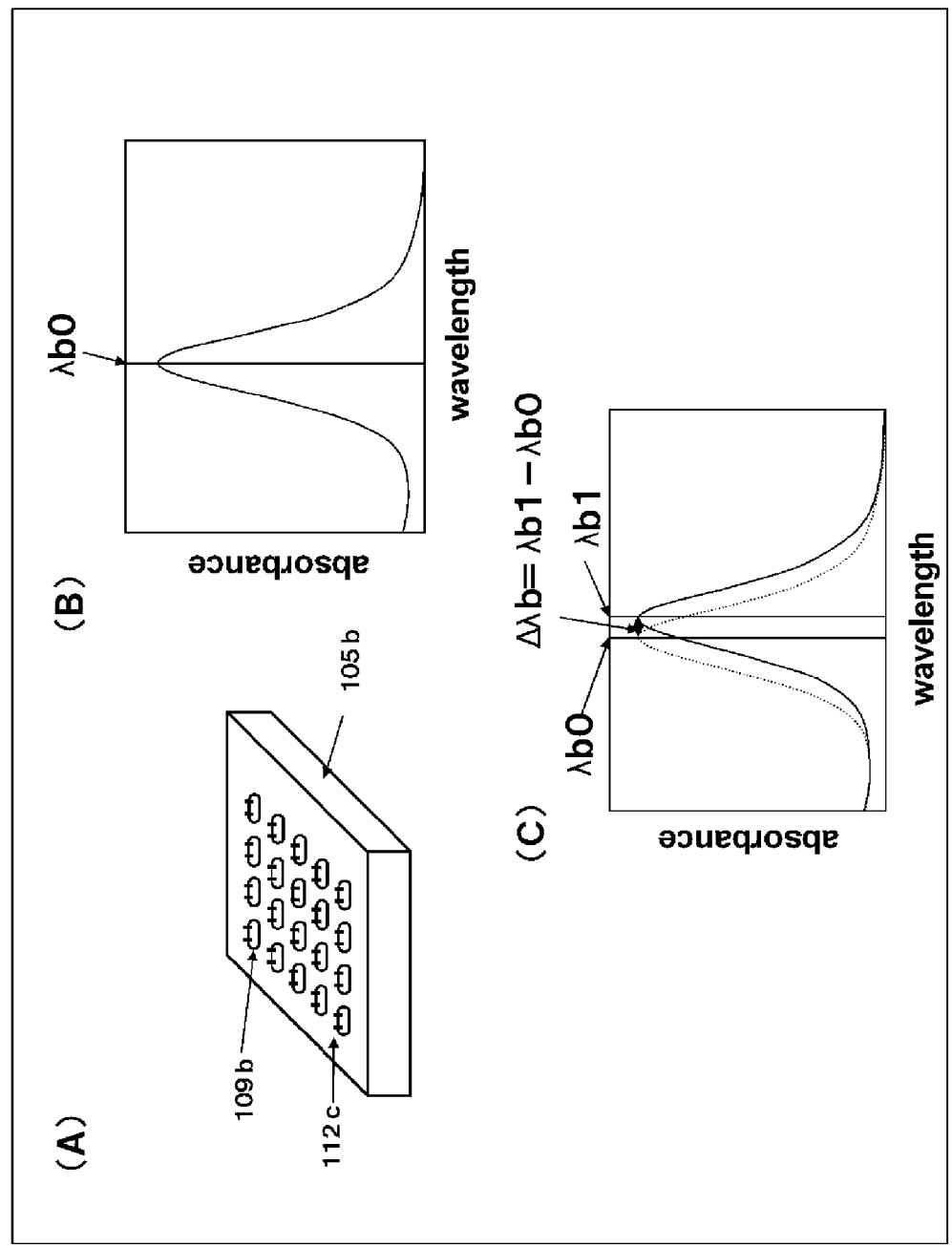
FIG. 19(A) is a configuration diagram of the second substrate 105b on which Au nanorods are formed such that the long axes thereof are aligned in the same direction.
FIG. 19(B) is a graph showing an absorption spectrum of the second substrate 105b when polarized light parallel to the long axes of the Au nanorods before test solution supply is applied thereto.
FIG. 19(C) is a graph showing an absorption spectrum of the second substrate 105b when the polarized light parallel to the long axes of the Au nanorods after test solution supply is applied thereto.

FIG. 17 is a perspective view of a part of the first substrate 605a of the cell 605 where the metallic nanorods are formed and a part of the second substrate 605b of the cell 605 where the metallic nanorods are formed. On the first substrate 605a, the first metallic nanorods 109a are formed such that the long axes thereof are aligned in the same direction. On the second substrate 605b, the second metallic nanorods 109b are formed such that the long axes thereof are aligned perpendicularly to the long axes of the first metallic nanorods 109a. The surface of the first substrate 605a on which the first metallic nanorods 109a are formed and the surface of the second substrate 605b on which the second metallic nanorods 109b are formed face in the opposite directions. The first metallic nanorods 109a are modified with the first antibody 112a, and the second metallic nanorods 109b are modified with the blocking substance 112c.

The operation of the biogenic substance concentration measuring apparatus according to the present embodiment is the same as that in Embodiment 1, and thus the description thereof is omitted. According to the present embodiment, a cell for biogenic substance concentration measurement is allowed to be provided which provides high measurement accuracy.

INDUSTRIAL APPLICABILITY

The biogenic substance concentration measuring apparatus according to the present invention is small in size and can measure a biogenic substance concentration with high accuracy, and thus is useful when the concentration of a test substance is low and a plurality of test substance concentrations are measured.

REFERENCE SIGNS LIST 100, 300 biogenic substance concentration measuring apparatus
101 halogen light source
102 lens
103 polarizing plate
104 lens
105, 205, 305, 405, 505, 605 cell
105a, 605a first substrate
105b, 605b second substrate
105c, 505c, 605c first spacer
105d, 505d, 605d second spacer
105e cover glass
105f, 505f, 605f first test solution retention space
105g, 505g, 605g second test solution retention space
105h substrate
106 slit
107 grating device
108 photodetector having a plurality of photo-receptive regions
109a, 109b, 109c metallic nanorod
110 microcomputer
111 memory
112a first antibody
112b second antibody
112c blocking substance
113 cog-wheel
114 shaft
115 motor
200, 400 optical measuring apparatus
205c spacer
205f test solution retention space
306 through-hole
313 cog-wheel
505a planar substrate
505b, 605e first cover glass
505e, 605h second cover glass
605i third spacer

The invention claimed is:

1. A method for measuring a concentration of a first antigen contained in a test solution, by using an apparatus for measuring a concentration of a biogenic substance, the method comprising the following steps (a) to (h):
   step (a) of preparing the apparatus,
   the apparatus comprising:
      a cell comprising therein a first region, a second region, and a space for retaining the test solution;
      a light source emitting a polarized light to the cell;
      a photoreceiver for receiving light which has passed through the cell along an optical axis that intersects the first region, the second region, and the space for retaining the test solution, wherein
      a plurality of first metallic nanorods each having a first antibody on a surface thereof are immobilized on the first region,
      a plurality of second metallic nanorods each having a blocking substance on a surface thereof are immobilized on the second region,
      the long axes of the plurality of first metallic nanorods are aligned in the same direction,
      the long axes of the plurality of second metallic nanorods are aligned in the same direction,
      the long-axis direction of the first metallic nanorods is orthogonal to the long-axis direction of the second metallic nanorods, and
      at least either one of the light source or the cell is rotatable about the optical axis;
   step (b) of supplying the test solution to the space for retaining the test solution to allow the first antigen to be bound to the first antibody and not to allow the first antigen to be bound to the blocking substance;
   step (c) of allowing polarized light parallel to the long-axis direction of the plurality of first metallic nanorods to pass through the cell along the optical axis to receive resultant first light with the photoreceiver;
   step (d) of calculating an amount $\Delta\lambda a$ of shift of a localized surface plasmon resonant wavelength caused by binding the first antigen to the antibody, on the basis of the first light;
   step (e) of rotating at least either one of the light source or the cell such that the polarized light is parallel to the long-axis direction of the plurality of second metallic nanorods;
   step (f) of allowing polarized light parallel to the long-axis direction of the plurality of second metallic nanorods to pass through the cell along the optical axis to receive resultant second light with the photoreceiver;
   step (g) of calculating an amount $\Delta\lambda b$ of shift of the localized surface plasmon resonant wavelength caused by supplying the test solution to the space for retaining the test solution, on the basis of the second light; and
   step (h) of calculating the concentration of the first antigen on the basis of a calibration curve and a difference represented by the following equation:

the difference=$\Delta\lambda a - \Delta\lambda b$.

2. The method according to claim 1, further comprising the following steps (i) and (j):
   step (i) of transmitting the polarized light parallel to the long-axis direction of the plurality of first metallic nanorods through the cell along the optical axis before the test solution is supplied to the space for retaining the test solution, so as to obtain third light; and step (j) of calculating a localized surface plasmon resonant wavelength $\lambda a0$ caused by the plurality of the first metallic nanorods before the test solution is supplied to the space for retaining the test solution, on the basis of the third light, wherein at step (d), a localized surface plasmon resonance wavelength $\lambda a1$ provided by binding the first antigen to the antibody is calculated, and the amount $\Delta \lambda a$ is obtained in accordance with the following equation:

$$\Delta \lambda a = \lambda a1 - \lambda a0.$$

3. The method according to claim 1, further comprising the following steps (i) and (j):

step i of transmitting the polarized light parallel to the long-axis direction of the plurality of second metallic nanorods through the cell along the optical axis before the test solution is supplied to the space for retaining the test solution, so as to obtain fourth light; and step j, of calculating a localized surface plasmon resonant wavelength $\lambda b0$ caused by the second metallic nanorods before the test solution is supplied to the space for retaining the test solution, on the basis of the fourth light, wherein at step (g), a localized surface plasmon resonance wavelength $\lambda b1$ provided by supplying the test solution to the space for retaining the test solution is obtained, and the amount $\Delta \lambda b$ is obtained in accordance with the following equation:

$$\Delta \lambda b = \lambda b1 - \lambda b0.$$

4. The method according to claim 2, further comprising the following steps (k) and (l):

step (k) of transmitting the polarized light parallel to the long-axis direction of the plurality of second metallic nanorods through the cell along the optical axis before the test solution is supplied to the space for retaining the test solution, to obtain fourth light; and step (l) of calculating a localized surface plasmon resonant wavelength $\lambda b0$ caused by the second metallic nanorods before the test solution is supplied to the space for retaining the test solution, on the basis of the fourth light, wherein at step (g), a localized surface plasmon resonance wavelength $\lambda b1$ provided by supplying the test solution to the space for retaining the test solution is obtained, and the amount $\Delta \lambda b$ is obtained in accordance with the following equation:

$$\Delta \lambda b = \lambda b1 - \lambda b0.$$

5. The method according to claim 1, wherein
the cell comprises a first substrate and a second substrate,
the first substrate has the first region on one surface thereof, and
the second substrate has the second region on one surface thereof.

6. The method according to claim 5, wherein the first region and the second region face in the same direction.

7. The method according to claim , wherein
a first spacer is disposed around the first region,
a cover is disposed so as to face the first substrate across the first spacer,
the first region, the first spacer, and the cover form a first space,
a second spacer is disposed around the second region,
the other surface of the first substrate, the second region, and the second spacer form a second space, and
the first space and the second space form the space for retaining the test solution.

8. The method according to claim 5, wherein the first region faces the second region.

9. The method according to claim 8, wherein
a spacer is disposed around the first region or around the second region, and
the first region, the second region, and the spacer form the space for retaining the test solution.

10. The method according to claim 5, wherein
a first spacer is disposed around the first region,
a first cover is disposed so as to face the first substrate across the first spacer,
the first region, the first spacer, and the first cover form a first space,
a second spacer is disposed around the second region,
a second cover is disposed so as to face the second substrate across the second spacer,
the second region, the second spacer, and the second cover form a second space, and
the first space and the second space form the space for retaining the test solution.

11. The method according to claim 1, wherein
the cell comprises a first substrate, and
the first substrate has the first region on one surface thereof and the second region on the other surface thereof.

12. The method according to claim 11, wherein
a first spacer is disposed around the first region,
a first cover is disposed so as to face the first substrate across the first spacer,
a second spacer is disposed around the second region,
a second cover is disposed so as to face the first substrate across the second spacer,
the first region, the first spacer, and the first cover form a first space,
the second region, the second spacer, and the second cover form a second space, and
the first space and the second space form the space for retaining the test solution.

13. The method according to claim 1, wherein the light source comprises a light source body and a polarizing plate for polarizing light emitting form the light source body.

14. The method according to claim 13, wherein the light source body is a halogen light.

15. The method according to claim 1, wherein the light source is a laser light source.

* * * * *